US011504292B2

(12) United States Patent
Takahashi et al.

(10) Patent No.: US 11,504,292 B2
(45) Date of Patent: Nov. 22, 2022

(54) GAIT MOTION ASSISTING DEVICE

(71) Applicants: Suncall Corporation, Kyoto (JP);
National University Corporation Kyoto Institute of Technology, Kyoto (JP); Kyoto University, Kyoto (JP)

(72) Inventors: Rei Takahashi, Kyoto (JP); Yukinobu Makihara, Tokyo (JP); Yuichi Sawada, Kyoto (JP); Yoshiyuki Higashi, Kyoto (JP); Tadao Tsuboyama, Kyoto (JP); Noriaki Ichihashi, Kyoto (JP); Koji Ohata, Kyoto (JP)

(73) Assignee: Suncall Corporation, Kyoto (JP)

( * ) Notice: Subject to any disclaimer, the term of this patent is extended or adjusted under 35 U.S.C. 154(b) by 387 days.

(21) Appl. No.: 16/756,136

(22) PCT Filed: Oct. 19, 2018

(86) PCT No.: PCT/JP2018/038974
§ 371 (c)(1),
(2) Date: Apr. 15, 2020

(87) PCT Pub. No.: WO2019/082802
PCT Pub. Date: May 2, 2019

(65) Prior Publication Data
US 2020/0297571 A1    Sep. 24, 2020

(30) Foreign Application Priority Data

Oct. 23, 2017   (JP) .............................. JP2017-204357

(51) Int. Cl.
*A61H 3/00* (2006.01)
*G16H 50/30* (2018.01)
*G16H 40/63* (2018.01)
*A61H 1/02* (2006.01)
*B25J 9/00* (2006.01)
*B25J 13/08* (2006.01)

(52) U.S. Cl.
CPC .............. *A61H 3/00* (2013.01); *A61H 1/024* (2013.01); *B25J 9/0006* (2013.01); *B25J 13/088* (2013.01);
(Continued)

(58) Field of Classification Search
CPC .... A61H 3/00; A61H 1/024; A61H 2201/165; A61H 2201/5007; A61H 2201/5069;
(Continued)

(56) References Cited

U.S. PATENT DOCUMENTS

2012/0259431 A1* 10/2012 Han .................... A61H 3/00
                                                    623/24
2015/0066156 A1   3/2015 Geyer et al.
(Continued)

FOREIGN PATENT DOCUMENTS

EP    3 156 010 A1    4/2017
EP    3 466 395 A1    4/2019
(Continued)

OTHER PUBLICATIONS

International Search Report issued in corresponding International Application No. PCT/JP2018/038974, dated Jan. 15, 2019.
(Continued)

*Primary Examiner* — Timothy A Musselman
(74) *Attorney, Agent, or Firm* — Sterne, Kessler, Goldstein & Fox P.L.L.C.

(57) ABSTRACT

The gait motion assisting device according to the present invention replicates movement of user's leg including thigh and lower leg around hip joint by pendulum movement of a rod-like rigid body, estimates hip joint angle and hip joint angular velocity of thigh calculated based on equation of motion of the pendulum movement by a state estimator using angle-related signal received from a thigh orientation detecting means as the observation, calculates the thigh phase angle using the estimated hip joint angle and the estimated hip joint angular velocity, and outputs assisting force having torque value calculated based on the thigh phase angle.

4 Claims, 15 Drawing Sheets

(52) U.S. Cl.
CPC ............ *G16H 40/63* (2018.01); *G16H 50/30* (2018.01); *A61H 2201/165* (2013.01); *A61H 2201/5007* (2013.01); *A61H 2201/5069* (2013.01); *A61H 2201/5079* (2013.01); *A61H 2201/5084* (2013.01); *G05B 2219/39188* (2013.01)

(58) Field of Classification Search
CPC ... A61H 2201/5079; A61H 2201/5084; G16H 40/63; B25J 9/0006; B25J 13/088; G05B 2219/39188
See application file for complete search history.

(56) References Cited

U.S. PATENT DOCUMENTS

| | | | | |
|---|---|---|---|---|
| 2015/0142130 | A1* | 5/2015 | Goldfarb | A61H 1/0244 623/25 |
| 2015/0190923 | A1 | 7/2015 | Seo et al. | |
| 2016/0338897 | A1 | 11/2016 | Takenaka et al. | |
| 2021/0298984 | A1* | 9/2021 | Bulea | A61H 1/0237 |

FOREIGN PATENT DOCUMENTS

| | | |
|---|---|---|
| JP | 2003-220584 A | 8/2003 |
| JP | 2007-260389 A | 10/2007 |
| JP | 5386253 B2 | 1/2014 |
| JP | 2014-073227 A | 4/2014 |
| JP | 5724312 B2 | 5/2015 |
| JP | 5799608 B2 | 10/2015 |
| JP | 2016-002408 A | 1/2016 |

OTHER PUBLICATIONS

Extended European Search Report issued in European Application No. 18870071.0, dated Aug. 9, 2021, 9 pages.

* cited by examiner

GAIT MOTION ASSISTING DEVICE

FIELD OF THE INVENTION

The present invention relates to a gait motion assisting device.

BACKGROUND ART

Gait motion assisting devices equipped with an actuator such as an electric motor for assisting movement of a leg are proposed as gait assistance or rehabilitation devices for people with leg disability or people with paralysis due to a stroke or the like (see Patent Literatures 1 to 3 below).

Specifically, conventional gait motion assisting devices as described in Patent Literatures 1 to 3 include a thigh-side brace to be attached to a thigh of a user, a lower leg-side brace to be attached to a lower leg of the user so as to be rotatable around a knee joint of the user relative to the thigh-side brace, an actuator attached to the thigh-side brace so as to be capable of imparting assisting force around the knee joint to the lower leg-side brace, a lower leg angle sensor for detecting the angle of rotation of the lower leg around the knee joint relative to the thigh, and a control device responsible for operational control of the actuator, and are configured such that the control device executes operational control of the actuator based on a detection signal from the lower leg angle sensor.

That is, the above conventional gait motion assisting devices are configured to identify a gait motion state based on the angle of rotation of the lower leg around the knee joint detected by the lower leg angle sensor, and perform operational control of the actuator so as to output assisting force having a size and a direction in accordance with the gait motion state.

However, during gait motion, the lower leg rotates around the knee joint while the thigh rotates around the hip joint.

That is, in the conventional configuration, the angle of rotation of the lower leg around the knee joint relative to the thigh that rotates around the hip joint is detected, and it is thus difficult to accurately identify a gait motion state.

Moreover, when a user is paralyzed by a stroke or the like, gait motion of the lower leg (forward and backward swing motion of the lower leg around the knee joint) often cannot be performed normally, while gait motion of the thigh (forward and backward swing motion of the thigh around the hip joint) can be performed relatively normally.

In such a case, with the conventional configuration, operational control of the actuator is performed based on the movement of the lower leg that is incapable of normal gait motion and, in this regard as well, there is a possibility that suitable gait assisting force cannot be provided.

Patent Literature 4 discloses a gait assisting device that identifies a gait motion state based on a thigh phase angle determined by the cyclic movement of the hip joint, and that performs operational control of an actuator so as to output gait assisting force to the thigh in accordance with the identified gait motion state.

Specifically, the gait assisting device described in Patent Literature 4 includes an imparting unit for imparting gait assisting force to the thigh, a control unit for performing operational control of the imparting unit, a detection unit for detecting at least one of a hip joint angle and a hip joint angular velocity, and a calculation unit for calculating the phase angle of the thigh based on the detection result of the detection unit, and is configured such that the control unit performs operational control of the imparting unit based on the phase angle.

Here, in Patent Literature 4, the phase angle of the thigh is calculated based on a hip joint angle detected by the detection unit and a hip joint angular velocity obtained by differentiating the hip joint angle.

In this configuration, noise components are emphasized due to differential processing, and it is difficult to obtain an accurate thigh phase angle.

In this regard, while it is possible to remove the noise components by performing low-pass processing on the signal detected by the detection unit, a time delay occurs in this case, which makes it difficult to perform operational control of the imparting unit at an appropriate timing.

PRIOR ART DOCUMENT

Patent Literature

Patent Literature 1: JP Patent No. 5724312
Patent Literature 2: JP Patent No. 5799608
Patent Literature 3: JP Patent No. 5386253
Patent Literature 4: JP 2016-002408

SUMMARY OF THE INVENTION

The present invention has been conceived in view of such conventional art, and an object of the present invention is to provide a gait motion assisting device capable of imparting suitable assisting force in response to a gait state during a gait cycle while effectively preventing or reducing a time delay.

In order to achieve the object, the present invention provides a gait motion assisting device including: an actuator for imparting assisting force to a gait motion of a user; a thigh orientation detecting means for detecting a hip joint angle-related signal relating to a hip joint angle that is a forward and backward swing angle of the user's thigh at each sampling timing; a thigh phase angle calculating means for calculating a thigh phase angle at one sampling timing k; an assisting torque calculating means having an output pattern data directly or indirectly defining a relationship between the thigh phase angle and a torque value that should be output by the actuator, wherein the assisting torque calculating means applies the thigh phase angle calculated by the thigh phase angle calculating means to the output pattern data to calculate a torque value that should be output at said one sampling timing k; and an operational control means responsible for operational control of the actuator so as to output assisting force having the torque value calculated by the assisting torque calculating means, wherein the thigh phase angle calculating means: replicates movement of the user's leg including a thigh and a lower leg around a hip joint in gait motion by pendulum movement of a rod-like rigid body having a predetermined length l, wherein a distal end part of the rod-like rigid body has a material point having a predetermined mass m and a proximal end part of the rod-like rigid body serves as a swing center, estimates the hip joint angle and a hip joint angular velocity approximately calculated based on an equation of motion in a direction tangential to a circle drawn along a swing trajectory of the material point by a state estimator using the angle-related signal received from the thigh orientation detecting means at the sampling timing k as an observation, and calculates the thigh phase angle at the sampling timing k using an estimated hip joint angle and an estimated hip joint angular velocity.

Since the gait motion assisting device according to the present invention replicates movement of the user's leg including the thigh and the lower leg around the hip joint by pendulum movement of the rod-like rigid body, estimates the hip joint angle and the hip joint angular velocity of the thigh calculated based on the equation of motion of the pendulum movement by the state estimator using the angle-related signal received from the thigh orientation detecting means as the observation, calculates the thigh phase angle using the estimated hip joint angle and the estimated hip joint angular velocity, and performs operational control of the actuator so as to output assisting force having the torque value calculated based on the thigh phase angle, the gait motion assisting device makes it possible to impart suitable assisting force in response to a gait state during a gait cycle while effectively preventing or reducing a time delay.

In one embodiment, the state estimator is a Kalman filter.

In this case, the thigh phase angle calculating means calculates the estimated hip joint angle and the estimated hip joint angular velocity using equation (1) based on the equation of motion, equation (1b) wherein the angle-related signal received from the thigh orientation detecting means is used as the observation, and equations (2a) to (2e) by the Kalman filter.

[Math. 1]

$$x[k+1] = Fx[k] + G_d \gamma[k] \quad (1a)$$

$$y[k] = Cx[k] + v[k] \quad (1b)$$

[Math. 2]

$$\hat{x}[k|k-1] = F\hat{x}[k-1|k-1] \quad (2a)$$

$$\hat{x}[k|k] = \hat{x}[k|k-1] + K[k]\{y[k] - C\hat{x}[k|k-1]\} \quad (2b)$$

$$K[k] = P[k|-1]C^T(CP[k|k-1]C^T + R)^{-1} \quad (2c)$$

$$P[k|k-1] = FP[k-1|k-1]F^T + G_d Q G_d^T \quad (2d)$$

$$P[k|k] = (I - K[k]C)P[k|k-1] \quad (2e)$$

Characters in equations (1a), (1b), and (2a) to (2e) are as follows, with a superscripted character T in the equations denoting matrix transposition operation.

[Math. 3]

$$x[k] = \begin{bmatrix} \theta[k] \\ \dot{\theta}[k] \end{bmatrix} \quad (3)$$

[Math. 4]

$$F = e^{A\Delta t} \quad (4)$$

[Math. 5]

$$G_d = \int_0^{\Delta t} e^{A\tau} G d\tau \quad (5)$$

[Math. 6]

$$A = \begin{bmatrix} 0 & 1 \\ -\frac{g}{\ell} & -\frac{\mu}{m\ell^2} \end{bmatrix} \quad (6)$$

[Math. 7]

$$G = \begin{bmatrix} 0 \\ \frac{1}{m\ell^2} \end{bmatrix} \quad (7)$$

θ: Hip joint angle
θ dot: Hip joint angular velocity
g: Gravitational acceleration
μ: Hip joint torque acting around hip joint during walking
Y: Unknown disturbance
v: Observation noise x hat [k|k]: Posteriori estimate at sampling timing k
x hat [k|k−1]: Priori estimate at sampling timing k
K[k]: Kalman gain at sampling timing k
P[k|k]: Posteriori error covariance matrix at sampling timing k
P[k|k−1]: Priori error covariance matrix at sampling timing k
y[k]: Observation (measure) of thigh orientation detecting means at sampling timing k
C: Observation matrix
Q: Covariance matrix of unknown disturbance y
R: Covariance matrix of observation noise v In one preferable embodiment, the thigh phase angle calculating means is configured to calculate a deviation between a swing center point of the estimated hip joint angle in a completed previous gait cycle and a hip joint angle zero point, perform a correction in accordance with the deviation on the angle-related signal received from the thigh orientation detecting means during a current gait cycle, and use a corrected angle-related signal as the observation of the state estimator.

The gait motion assisting device according to the present invention may include a thigh-side brace to be attached to the user's thigh, and a lower leg-side brace to be attached to the user's lower leg so as to be rotatable around the user's knee joint, wherein the actuator is attached to the thigh-side brace and is capable of imparting assisting force around the knee joint to the lower leg-side brace.

EMBODIMENT FOR CARRYING OUT THE INVENTION

Below, one embodiment of the gait motion assisting device according to the present invention will now be described with reference to the attached drawings.

Figure 1:
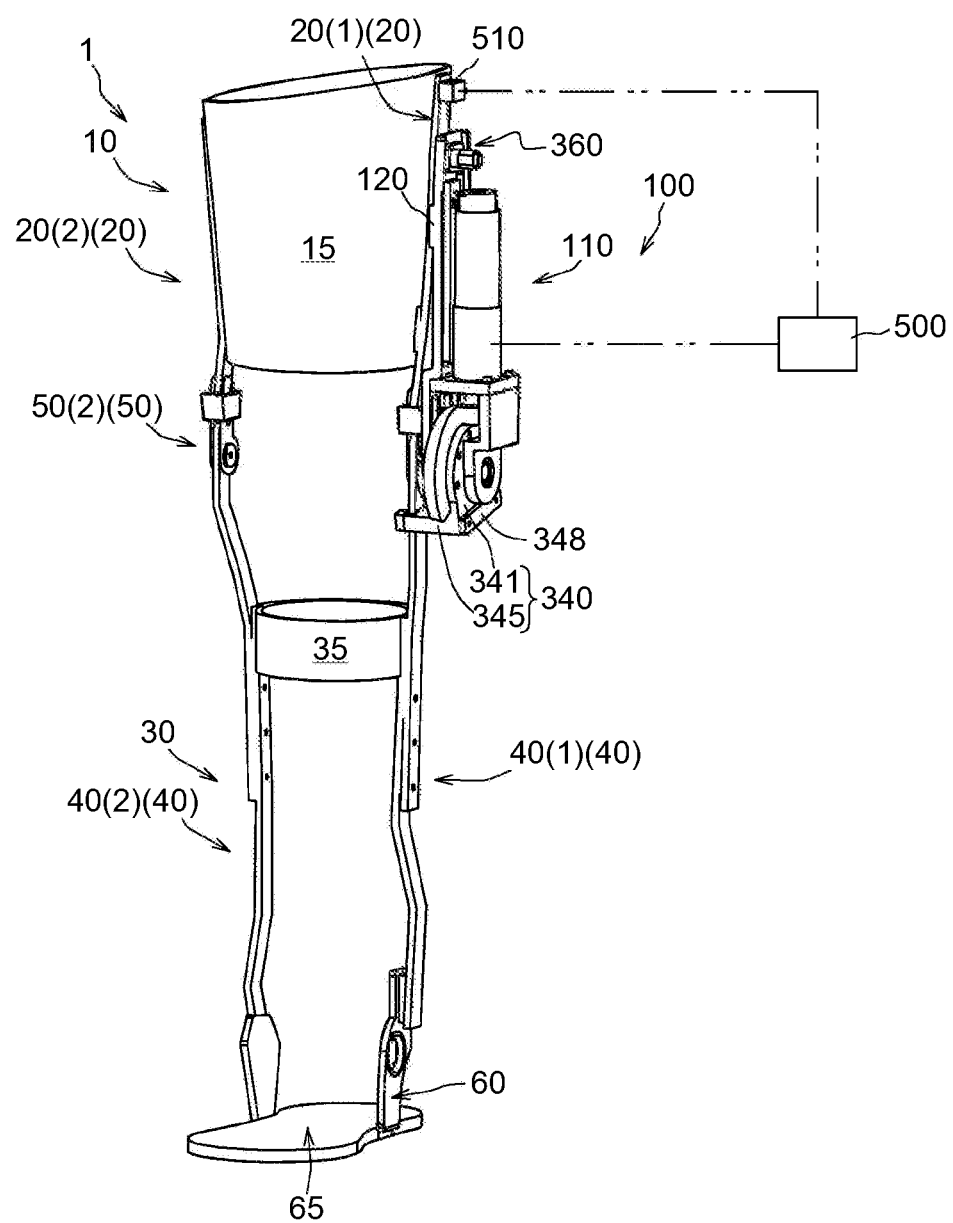
FIG. 1 is a perspective view of a gait motion assisting device according to one embodiment of the present invention.
Figure 2:
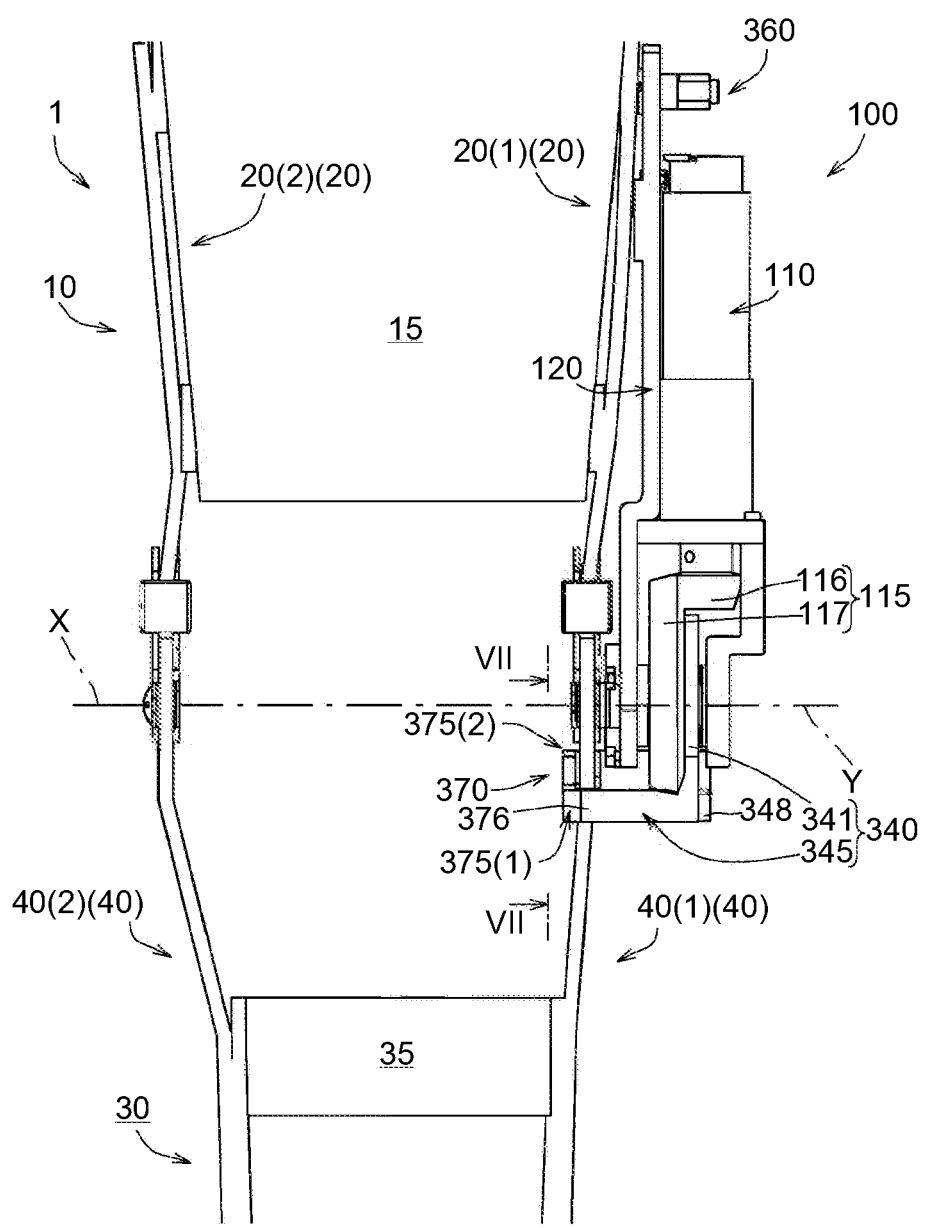
FIG. 2 is a partial front view of the gait motion assisting device.

FIGS. 1 and 2 respectively show a perspective view and a partial front view of the gait motion assisting device 1 according to the present embodiment, respectively.

Figure 3:
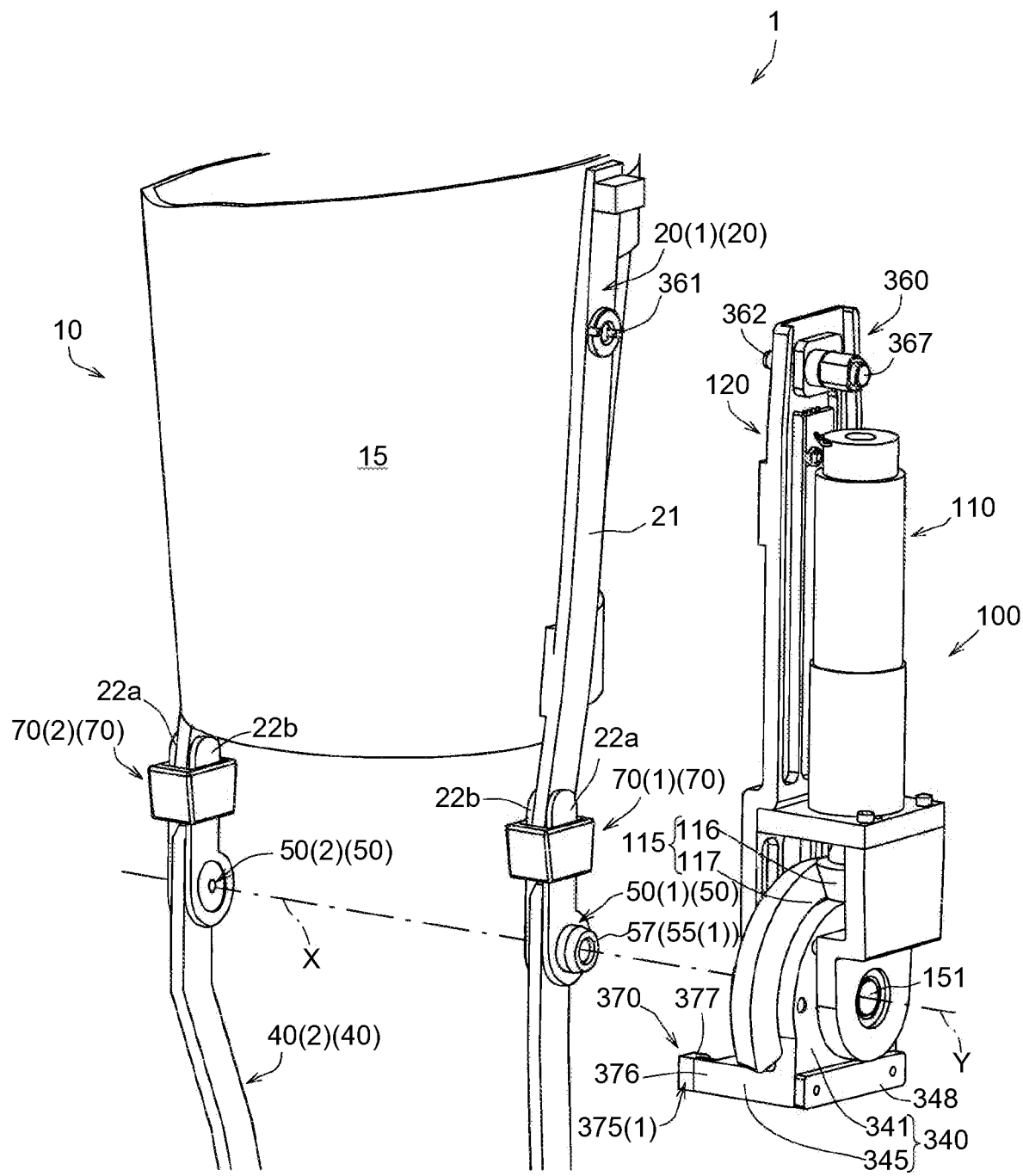
FIG. 3 is a partially exploded perspective view of the gait motion assisting device as viewed from the outer side in the user width direction.
Figure 4:
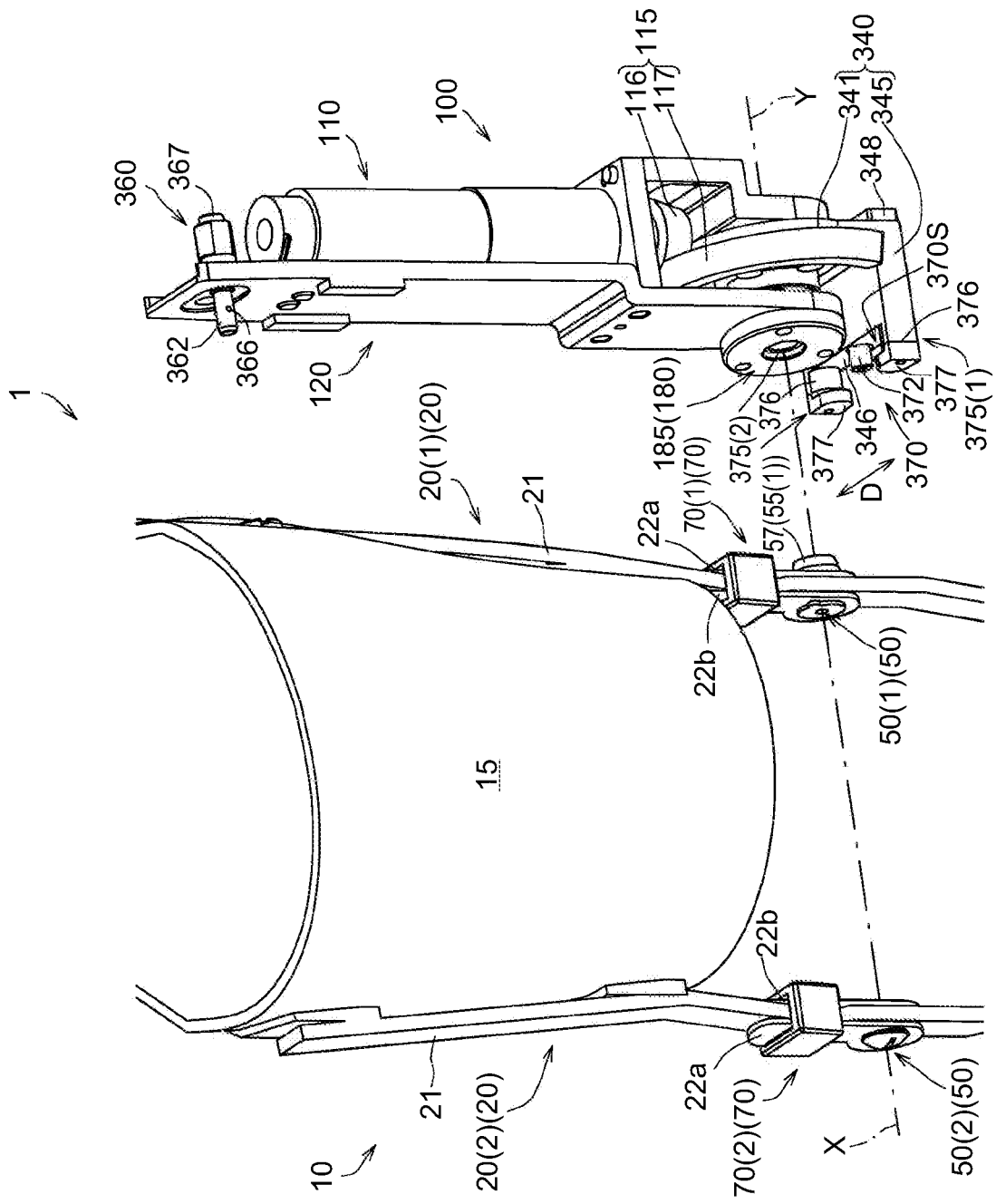
FIG. 4 is a partially exploded perspective view of the gait motion assisting device as viewed from the inner side in the user width direction.

Also, FIGS. 3 and 4 respectively show partially exploded perspective views of the gait motion assisting device 1 as viewed from the outer side and the inner side in the user width direction.

The gait motion assisting device 1 is a device that people with leg disability or people with paralysis due to a stroke or the like wears for gait assistance or rehabilitation, and is configured to impart assisting force for gait motion by an actuator unit 100 attached thereto.

The gait motion assisting device 1 is configured to impart assisting force by the actuator unit 100 to the user's lower leg.

Specifically, as shown in FIGS. 1 to 4, the gait motion assisting device 1 has a thigh-side brace 10 to be attached to the user's thigh, a lower leg-side brace 30 to be attached to the user's lower leg, and the actuator unit 100 attached to the thigh-side brace 10 so as to be capable of imparting assisting force around the knee joint to the lower leg-side brace 30.

In the present embodiment, the thigh-side brace 10 has a thigh attachment 15 to be attached the user's thigh, and a thigh frame 20 connected to the thigh attachment 15.

The thigh attachment 15 may take various forms as long as it is attachable to the user's thigh.

In the present embodiment, as shown in FIG. 1, the thigh attachment 15 is in a cylindrical form having an attachment hole with such a size that the user's thigh can be inserted in a fitted manner.

As shown in FIGS. 1 to 4, the thigh frame 20 has a first thigh frame 20(1) vertically extending along the user's thigh on the outer side in the user width direction.

In the present embodiment, as shown in FIGS. 1 to 4, the thigh frame 20 further has a second thigh frame 20(2) vertically extending along the user's thigh on the inner side in the user width direction so as to be opposed to the first thigh frame 20(1), with the user's thigh inserted in the thigh attachment 15 in-between.

In the present embodiment, the lower leg-side brace 30 has a lower leg attachment 35 to be attached the user's lower leg, and a lower leg frame 40 connected to the lower leg attachment 15.

The lower leg attachment 35 may take various forms as long as it is attachable to the user's lower leg.

In the present embodiment, as shown in FIG. 1, the lower leg attachment 35 is in a cylindrical form having an attachment hole with such a size that the user's lower leg can be inserted in a fitted matter.

As shown in FIGS. 1 to 4, the lower leg frame 40 has a first lower leg frame 40(1) vertically extending along the user's lower leg on the outer side in the user width direction.

In the present embodiment, as shown in FIGS. 1 to 4, the lower leg frame 40 further has a second lower leg frame 40(2) vertically extending along the user's lower leg on the inner side in the user width direction so as to be opposed to the first lower leg frame 40(1), with the user's lower leg inserted in the lower leg attachment 35 in-between.

In the present embodiment, the lower leg-side brace 30 further has a foot attachment 65 on which the used place a foot, and a foot frame 60 that supports the foot attachment 65 and is connected to the lower leg frame 40.

The lower leg-side brace 30 is connected to the connects the thigh-side brace 10 so as to be rotatable relative to the thigh-side brace 10 around the swing axis of the user's knee joint.

That is, the lower leg frame 40 is connected to the thigh frame 20 so as to be rotatable relative to the thigh frame 20 around a swing axis X of the user's knee joint.

As described above, in the present embodiment, the thigh frame 20 has the first and second thigh frames 20(1), 20(2), and the lower leg frame 40 has the first and second lower leg frames 40(1), 40(2).

Accordingly, the first leg frames 40(1) is connected to the first thigh frames 20(1) so as to be rotatable relative to the first thigh frame 20(1) around the swing axis X, and the second leg frames 40(2) is connected to the second thigh frames 20(2) so as to be rotatable relative to the second thigh frame 20(2) around the swing axis X.

Figure 5:
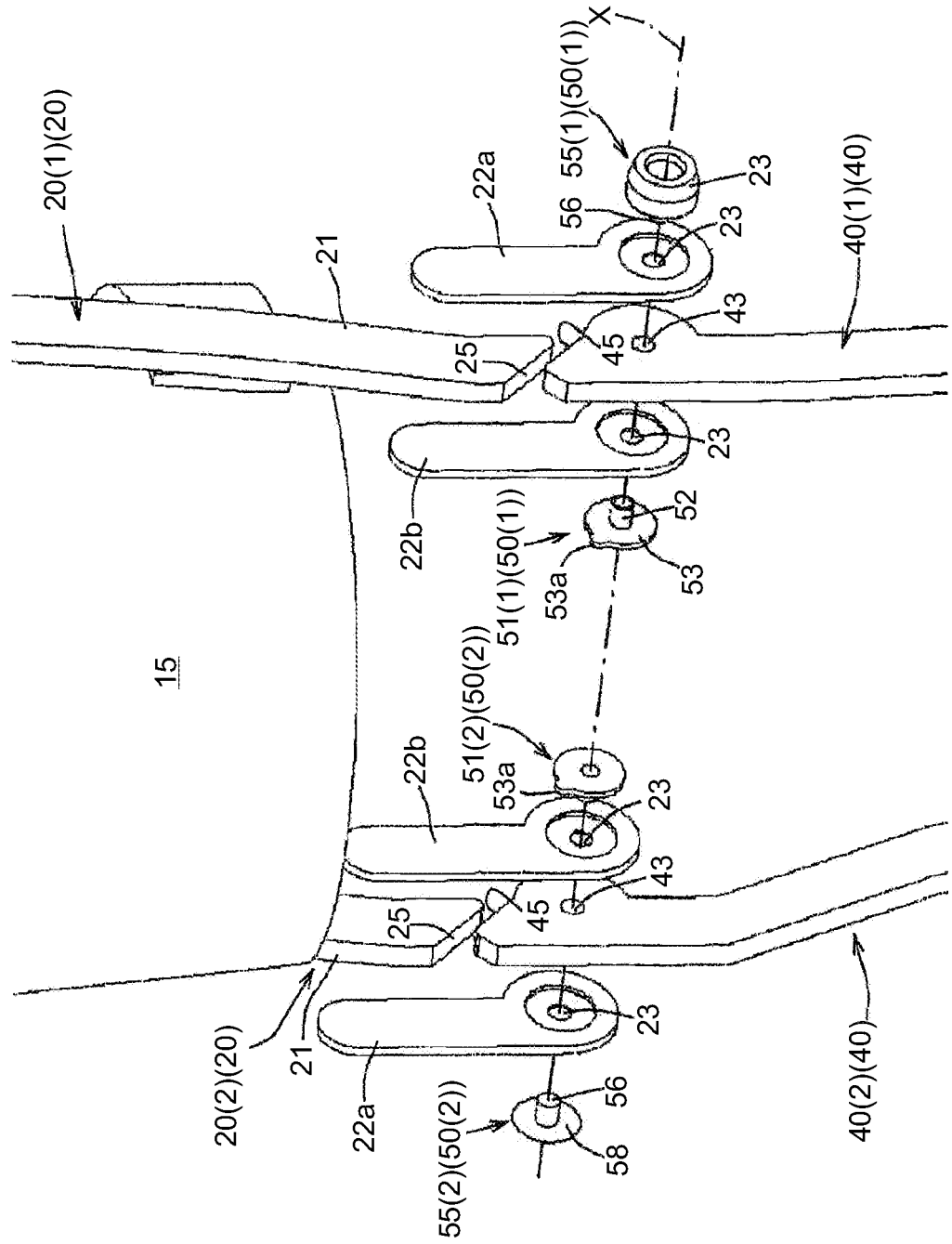
FIG. 5 is an exploded perspective view of a thigh frame and a lower leg frame of the gait motion assisting device.

FIG. 5 shows an exploded perspective view of the thigh frame 20 and the lower leg frame 40.

As shown in FIG. 5, the thigh frame 20 has a vertically extending thigh frame main body 21 and a pair of connecting pieces 22a, 22b fixed to the thigh frame main body 21 so as to sandwich a lower end part of the frame main body 21 by pinning, welding, or the like.

The pair of connecting pieces 22a, 22b include an outer side connecting piece 22a that is positioned on a side farther away from the user's leg than the thigh frame main body 21 is, and an inner side connecting piece 22b that is positioned on a side closer to the use's leg than the thigh frame main body 21 is.

The lower leg frame 40 is inserted between the pair of connecting pieces 22a, 22b and is connected thereto so as to be rotatable around the swing axis X.

Specifically, the pair of connecting pieces 22a, 22b and the upper end part of the lower leg frame 40 are formed with attachment holes 23, 43 that are coaxially with the swing axis X and along the user width direction.

The first thigh frame 20(1) and the first lower leg frame 40(1), which are positioned on a side to which the actuator unit 100 is attached (on the outer side in the user width direction relative to the user's corresponding leg), are connected to each other via a first swinging connector 50(1) so as to be rotatable around the swing axis X.

The first swinging connector 50(1) has a first internally threaded member 51(1) and a first externally threaded member 55(1) separably screwed to each other in the attachment holes 23, 43.

The first internally threaded member 51(1) has a cylindrical part 52 to be inserted into the attachment hole 23 from a side on which the inner side connecting piece 22b is positioned, and a flange part 53 extending more radially outward from a portion of the cylindrical part 52 that is positioned closer to the user's leg than the attachment hole 23. The cylindrical part 52 has a screw hole that is open toward the free end side.

The first externally threaded member 55(1) has a cylindrical part 56 to be screwed into the attachment hole 23 from a side on which the outer side connecting piece 22a is positioned, and an engagement projection 57 extending from a portion of the cylindrical part 56 that is positioned farther away from the user's leg than the attachment hole 23.

The cylindrical part 56 of the first externally threaded member 55(1) is formed with an external thread to be screwed into the screw hole of the first internally threaded member 51(1) within the attachment holes 23, 43.

The first lower leg frame 40(1) is connected to the first thigh frame 20(1) so as to be rotatable by threadedly inserting the external thread formed in the first internally threaded member 55(1) into the screw hole of the first internally threaded member 51(1) within the attachment holes 23, 43.

The second thigh frame 20(2) and the second lower leg frame 40(2), which are positioned on the inner side in the user width direction relative to the user's corresponding leg), are connected to each other via a second swinging connector 50(2) so as to be rotatable around the swing axis X.

The second swinging connector 50(2) has a second internally threaded member 51(2) and a second externally threaded member 55(2) separably screwed to each other in the attachment holes 23, 43.

The second internally threaded member 51(2) has the configuration same as the first internally threaded member 51(1).

The second externally threaded member 55(2) has a cylindrical part 56 to be screwed into the attachment hole 23 from a side on which the outer side connecting piece 22a is positioned, and a flange part 58 extending more radially outward from a portion of the cylindrical part 56 that is positioned more inward in the user width direction than the attachment hole 23.

The cylindrical part 56 of the second externally threaded member 55(2) is formed with an external thread to be screwed into the screw hole of the second internally threaded member 51(2) within the attachment holes 23, 43.

The second lower leg frame 40(2) is connected to the second thigh frame 20(2) so as to be rotatable by threadedly inserting the external thread formed in the second internally threaded member 55(2) into the screw hole of the second internally threaded member 51(2) within the attachment holes 23, 43.

Reference number 53a in FIG. 5 is a radially outward projection that is provided on the flange part 53 and that engages with a depression formed in the inner connecting piece 22b, and thereby the internally threaded member 51 is retained so as to be incapable of relative rotation around the axis relative to the inner connecting piece 22b (i.e., the thigh frame 20).

In the present embodiment, as shown in FIGS. 1 to 4, the gait motion assisting device 1 further has a locking member 70 for inhibiting the rotation of the lower leg frame 40 around the swing axis X relative to the thigh frame 20.

The locking member 70 is configured so as to be capable of reaching a locked state (the state shown in FIGS. 1 to 4) where the thigh frame 20 and the lower leg frame 40 are surrounded by the locking member 70 to connect both frames 20, 40 and prevent the lower leg frame 40 from being relatively rotated around the swing axis X relative to the thigh frame 20, and a cancelled state where connection between the thigh frame 20 and the lower leg frame 40 is cancelled to permit the lower leg frame 40 to be relatively rotated around the swing axis X relative to the thigh frame 20.

In the present embodiment, the locking member 70 has a first locking member 70(1) positioned on the outer side in the user width direction and acting on the first thigh frame 20(1) and the first lower leg frame 40(1), and a second locking member 70(2) positioned on the inner side in the user width direction and acting on the second thigh frame 20(2) and the second lower leg frame 40(2).

In the present embodiment, as shown in FIG. 5, an upper-end surface 45 of the lower leg frame 40 (the end surface facing the thigh frame 20) is a sloped surface such that the radial distance from the swing axis X increases from one side toward the other side around the swing axis X, and a lower-end surface 25 of the thigh frame 20 (the end surface facing the lower leg frame 40) is a sloped surface corresponding to the upper-end surface 45 of the lower leg frame 40.

Due to this configuration, the lower leg frame 40 rotates only toward one side around the swing axis X relative to the thigh frame 20 (in the direction in which the user's lower leg is bent relative to the thigh), and does not rotates toward the other side beyond a predetermined relative angle to the thigh frame 20 while allowing the user's lower leg to be extended relative to the thigh until the predetermined relative angle.

Figure 6:
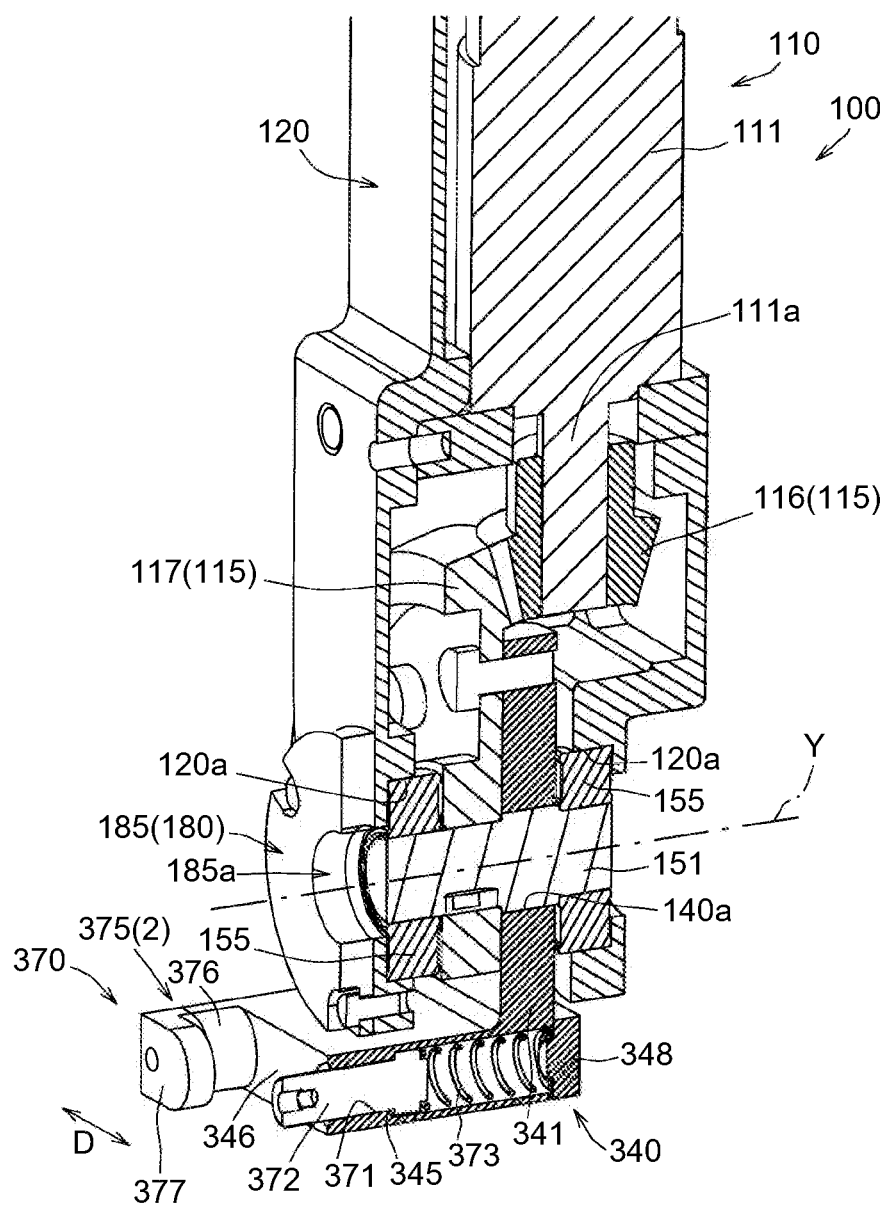
FIG. 6 is a partially enlarged vertical cross-sectional view of an actuator unit of the gait motion assisting device.

FIG. 6 is a partially enlarged vertical cross-sectional view of the actuator unit 100.

As shown in FIGS. 1 to 4 and 5, the actuator unit 100 includes an upper frame 120, a lower frame 340 connected to the upper frame 120 so as to be rotatable around a pivot axis Y, a driver 110 such as an electric motor for producing driving force for rotating the lower frame 340 around the pivot axis Y, an upper connecting body 360 for connecting the upper frame 120 to the thigh frame 20, a rotation center connecting body 180 for positioning the pivot axis Y coaxially with the swing axis X, and a lower connecting body 370.

The upper frame 120 and the lower frame 340 are provided with an upper frame attachment hole 120a and a lower frame attachment hole 140a coaxially with the pivot axis Y, respectively.

A rotational connecting shaft 151 is fixed to the lower frame attachment hole 140a. The rotational connecting shaft 151 is supported by the upper frame attachment hole 120a through bearing members 155 in a rotatable manner around an axis so that the lower frame 340 is connected to the upper frame 120 so as to be rotatable around the pivot axis Y.

The driver 110 has a driving source 111 such as an electric motor, and a transmission mechanism 115 for transmitting driving force produced by the driving source 111 to the lower frame 340.

The driving source 111 is fixed to an outer side surface of the upper frame 120.

In the present embodiment, as shown in FIG. 6, the driving source 111 is fixed to the outer side surface of the upper frame 120, with an output shaft 111a extending downward.

In the present embodiment, as shown in FIG. 6, the transmission mechanism 115 has a drive-side bevel gear 116 supported by the output shaft 111a so as to be incapable of relative rotation, and a driven-side bevel gear 117 that is connected to the lower frame 140 so as to be incapable of relative rotation around the pivot axis Y and that is meshed with the drive-side bevel gear 116.

The actuator unit 100 may include a sensor (not shown) for detecting a rotational angle around the axis of the rotational connecting shaft 151.

Detecting the rotational angle around the axis of the rotational connecting shaft 151 by the sensor enables the swinging angle of the lower frame 340 around the pivot axis Y to be recognized.

As shown in FIGS. 3 and 4, the upper connecting body 360 has an engagement hole 361 formed in the first thigh frame 20(1) so as to be parallel to the pivot axis Y and be opened outward in the user width direction (toward the upper frame 120), and an engagement pin 362 provided in the upper frame so as to be capable of be engaged into the engagement hole 361.

In the present embodiment, the upper connecting body 360 includes a locking mechanism.

As shown in FIG. 4, the locking mechanism includes a projection 366 capable of radially advancing and retreating relative to an outer surface of the engagement pin 362 so as to take an engagement position in which the projection 366 projects radially outward from the outer surface of the engagement pin and a release position in which the projection 366 is retreated into the engagement pin, a biasing member (not shown) for pressing the projection 366 toward the engagement position, a depression (not shown) provided in the engagement hole such that the projection 366 is engaged into the depression when the engagement pin 362 is inserted in the engagement hole 361, and a release operation part 367 for pressing the projection 360 to the release position against the biasing force of the biasing member in response to manual operation from outside.

As shown in FIGS. 4 and 6, the rotation center connecting body 180 includes a brace-side rotation center connecting member provided in the first thigh frame 20(1) or the first lower leg frame 40(1) so as to be positioned coaxially with the swing axis X, and an actuator-side rotation center connecting member 185 provided in the upper frame 120 or lower frame 340 so as to be positioned coaxially with the pivot axis Y.

In the present embodiment, the engagement projection 57 of the first swinging connector 50(1) acts as the brace-side rotation center connecting member.

The actuator-side rotation center connecting member 185 has an actuator-side depression/projection engagement part 185a that detachably depression/projection-engages with the brace-side rotation center connecting member (the engagement projection 57 in the present embodiment).

In the present embodiment, as shown in FIG. 6, the upper frame 120 is formed with an engagement depression in which the brace-side rotation center connecting member (the engagement projection 57 in the present embodiment) is detachably and rotatably around the axis engaged. The engagement depression acts as the actuator-side depression/projection engagement part 185a.

As shown in FIGS. 3, 4 and 6, the lower connecting body 370 connects the lower frame 340 to the first lower leg frame 40(1) such that the first lower leg frame 40(1) is rotated around the swing axis X relative to the first thigh frame 20(1) in response to the rotational movement of the lower frame 340 around the pivot axis Y relative to the upper frame 120.

Specifically, as shown in FIG. 6, the lower frame 340 has a proximal end part 341 connected to the upper frame 120 via the rotational connecting shaft 151 so as to be rotatable around the pivot axis Y, and a distal end part 345 extending from the proximal end part 341 toward the first lower leg frame 40(1).

As shown in FIG. 6 or the like, in the present embodiment, the proximal end part 341 supports the driven-side bevel gear 117 so as to be integrally rotated around the pivot axis Y and, thereby, the driven-side bevel gear 117 and the proximal end part 341 are integrally rotated around the pivot axis Y by rotational power from the driver 110.

In the present embodiment, the proximal end part 341 is in a substantially upright flat plate form.

As shown in FIGS. 4 and 6, a distal end surface 346 of the distal end part 345 forms an opposing surface facing the outer surface of the first lower leg frame 40(1) facing outward in the user width direction.

The distal end surface 346 has a predetermined length in a width direction D corresponding to the width direction of the first lower leg frame 40(1) (i.e., the user front-back direction).

In the present embodiment, the distal end part 345 is in a substantially horizontal flat plate form, and the distal end surface 346 is substantially rectangular.

As shown in FIGS. 4 and 6, the lower connecting body 370 has a support hole 371 formed in the distal end part 345, an engagement pin 372 accommodated in the support hole 371 so as to capable of advancing and retreating, a biasing spring 373 for biasing the engagement pin 372, and an engagement arm 375 provided on the distal end part 375.

The support hole 371 is open to the opposing surface in an intermediate region in the width direction of the opposing surface and extends in a direction substantially perpendicular to the outer surface of the first lower leg frame 40(1).

The engagement pin 372 is accommodated in the support hole 371 so as to be axially movable such that the distal end can take a projecting position where the distal end projects from the opposing surface and a retreated position where the distal end is in the support hole 371 so as to be away from the first lower leg frame 40(1).

The biasing spring 373 biases the engagement pin 371 toward the projecting position.

In the present embodiment, the biasing spring 373 is interposed between the proximal end part of the engagement pin 372 and the back surface of the support hole 371.

Specifically, in the present embodiment, the support hole 371 is formed in the distal end part 345 such that one end side is open to the opposing surface and the other end side is open to the back surface opposite the opposing surface, and the other end side of the support hole 371 is closed by a closing plate 348 fixed to the back surface of the distal end part 345. In this case, the closing plate 348 forms the back surface of the support hole 371.

The engagement arm 375 has an axially extending part 376 extending along the pivot axis Y from the opposing surface toward the first lower leg frame 40(1).

A width-direction separating distance between the axially extending part 376 and the engagement pin 372 is set such that the first lower leg frame 40(1) can be disposed between the axially extending part 376 and the engagement pin 372 with respect to the width direction of the lower frame 340.

That is, the width-direction separating distance between the engagement pin 372 and the axially extending part 376 is greater than the width of the first lower leg frame 40(1) such that the first lower leg frame 40 (1) can be positioned between the engagement pin 372 and the axially extending part 376 with respect to the user front-back direction.

Here, an operation for attaching the lower frame 340 to the first lower leg frame 40(1) by the lower connecting body 370 will now be described.

Figure 7:
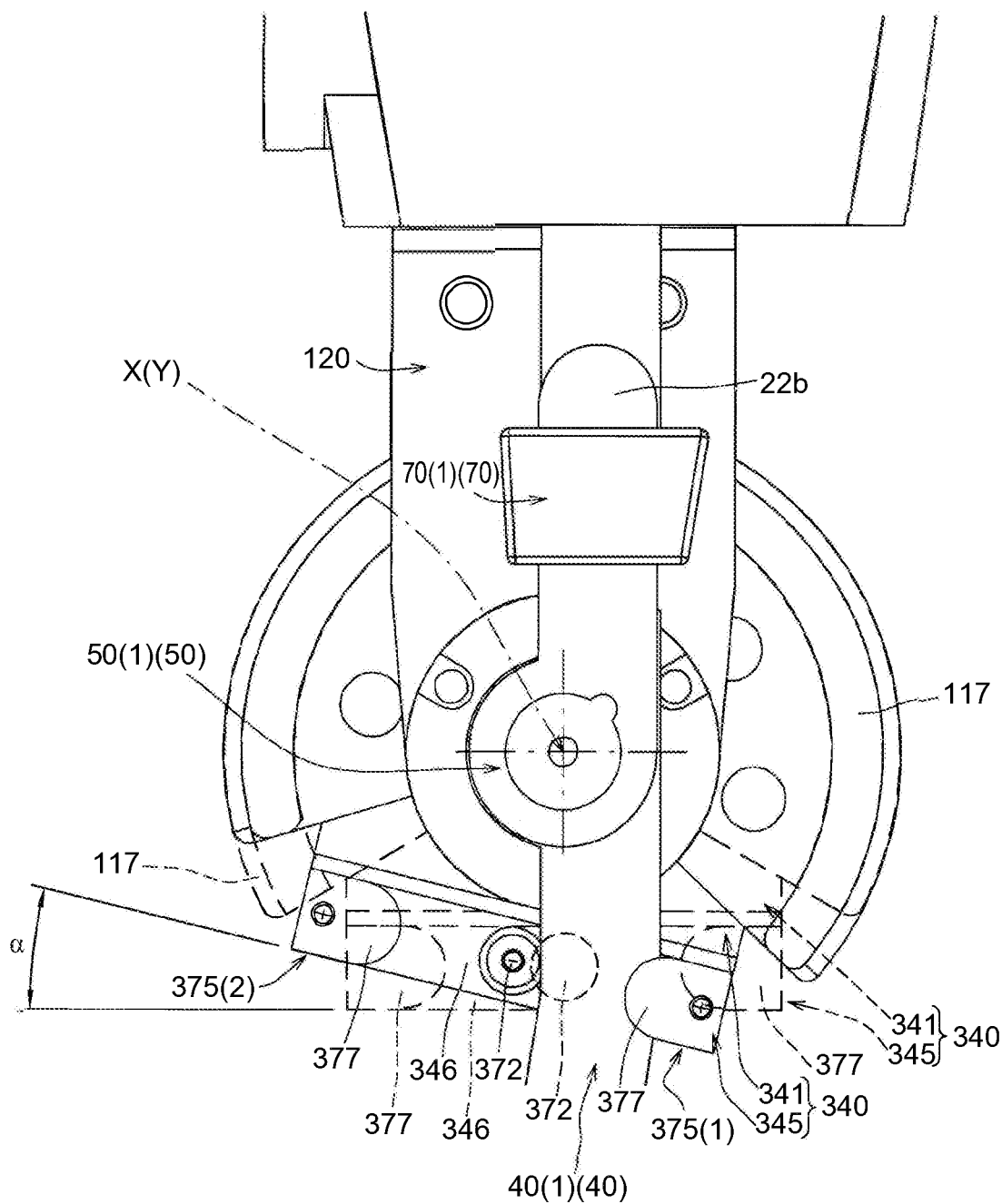
FIG. 7 is an end view taken along the line VII-VII in FIG. 2.

FIG. 7 shows an end view taken along the line VII-VII in FIG. 2.

When connecting the lower frame 340 to the first lower leg frame 40(1) by the lower connecting body 370, first the actuator unit 100 is relatively moved in the pivot axis Y direction to a position where the first lower leg frame 40(1) overlaps the axially extending part 376 with respect to the direction parallel to the pivot axis Y, while positioning the engagement pin 372 in the retreated position against the biasing force of the biasing spring 373.

At this time, preferably, movement of the engagement pin 372 to the retreated position can be performed via the outer surface of the first lower leg frame 40(1).

That is, the actuator unit 100 can be relatively moved toward the first lower leg frame 40(1) such that the engagement pin 372 is moved from the projecting position to the retreated position, with the outer surface of the first lower leg frame 40(1) being in contact with the engagement pin 372. This state is indicated by broken lines in FIG. 7.

From the state indicated by broken lines in FIG. 7, rotating the lower frame 340 in a connecting direction around the pivot axis Y (the clockwise direction in FIG. 7) cancels contact between the engagement pin 372 and the first lower leg frame 40(1), and brings the engaging pin 372 from the retreated position to the projecting position due to the biasing force of the biasing spring 373.

Accordingly, the first lower leg frame 40(1) is sandwiched between the engagement pin 372 and the axially extending part 376 with respect to the width direction of the lower frame 340 (the user front-back direction) (see solid lines in FIG. 7). Thus, with the lower frame 340 being relatively movable in the longitudinal direction of the frame relative to the first lower leg frame 40(1), an interlocking state is attained where the first lower leg frame 40(1) is rotated around the swing axis X relative to the thigh frame 20 in conjunction with the rotational movement of the lower frame 340 around the pivot axis Y relative to the upper frame 120.

By reversing the operation performed during attachment, the lower frame 340 connected to the first lower leg frame 40(1) by the lower connecting body 370 can be detached.

That is, when the lower frame 340 is connected to the first lower leg frame 40(1) by the lower connecting body 370, the engagement pin 372 is positioned in the projecting position due to the biasing force of the biasing spring 373.

By pressing the engagement pin 372 in the projecting position to the retreated position against the biasing force of the biasing spring 373 by manual operational force and rotating the lower frame 340 in the cancelling direction around the pivot axis Y (the counterclockwise direction in FIG. 7), a state where the distal end part of the engagement pin 372 is in contact with the outer surface of the first lower leg frame 40(1) is attained (the state indicated by broken lines in FIG. 7).

Thereafter, by relatively moving the first lower leg frame 40(1) and the lower frame 340 in mutually separating directions, the lower frame 340 can be detached from the first lower leg frame 40(1).

Preferably, the engagement arm 375 includes a width-direction extending part 377 extending from the axially extending part 376 toward the engagement pin 372 with respect to a width direction W of the opposing surface and facing the inner surface of the first lower leg frame 40(1) (the side surface facing inward relative to the user width direction), with the lower frame 340 being connected to the first lower leg frame 40(1).

The width-direction extending part 377 is configured such that the axially separating distance between the width-direction extending part 377 and the distal end surface 346 is greater than the thickness of the first lower leg frame 40(1) such that the first lower leg frame 40(1) can be disposed in a retaining space 370S (see FIG. 4) surrounded by the engagement pin 372, the distal end surface 346 forming the opposing surface, the axially extending part 376 and the width-direction extending part 377.

By providing the engagement arm 375 with the width-direction extending part 377, the lower frame 340 and the first lower leg frame 40(1) can be effectively prevented from relatively moving away from each other in the pivot axis Y directions in the state where the lower frame 340 is connected to the first lower leg frame 40(1) by the lower connecting body 370. Accordingly, unintentional detachment of the lower frame 340 from the first lower leg frame 40(1) can be effectively prevented.

In the present embodiment, the engagement arm 375 has first and second engagement arms 375(1), 375(2) respectively provided on one side and the other side in the width direction of the opposing surface, and is capable of connecting the lower frame 340 to the first lower leg frame 40(1) even when the lower frame 340 is rotated in any direction around the pivot axis Y from the state indicated by broken lines in FIG. 7.

In the present embodiment, as shown in FIG. 7, the swing axis X is off-center toward one side in the width direction (the user front-back direction) of the first lower leg frame 40(1) relative to the center in the width direction (the user front-back direction) of the first lower leg frame 40(1). In FIG. 7, the swing axis X is off-center toward the back with respect to the user front-back direction relative to the width direction center of the first lower leg frame 40(1).

As in this case, the actuator unit 100 can be attached to any of the left foot side and the right foot side of the gait motion assisting device 1 by disposing the engagement pin 372 in the center in the width direction (the user front-back direction) of the lower frame 140, and configuring the engagement arm 375 to have the first and second engagement arms 375(1), 375(2) that are respectively positioned on one side and the other side in the width direction of the lower frame 140 (the front side and the back side with respect to the user front-back direction), with the engagement pin 372 in-between.

That is, when attaching the actuator unit 100 to the left foot side of the gait motion assisting device 1, the first lower leg frame 40(1) can be sandwiched between the engagement pin 372 and the first engagement arm 375(1), and when attaching the actuator unit 100 to the right foot side of the gait motion assisting device 1, the first lower leg frame 40(1) can be sandwiched between the engagement pin 372F and the second engagement arm 375(2).

In the present embodiment, as shown in FIG. 7, the actuator unit 100 is attached to the gait motion assisting device 1 such that the first lower leg frame 40(1) is sandwiched between the engagement pin 372 and the first engagement arm 375(1) positioned on the front side with respect to the user front-back direction, but when it is desired to increase the rotational angle of the first lower leg frame 40(1) relative to the first thigh frame 20(1), the actuator unit 100 can be attached to the gait motion assisting device 1 such that the first lower leg frame 40(1) is sandwiched between the engagement pin 372 and the second engagement arm 375(2) positioned on the back side with respect to the user front-back direction.

That is, when the first lower leg frame 40(1) is sandwiched between the engagement pin 372 and the first engagement arm 375(1) positioned on the front side with respect to the user front-back direction, the initial orientation of the lower frame 340 (the orientation of the lower frame 340 when a user is in substantially upright posture with the actuator unit 100 being attached, and the orientation indicated by solid lines in FIG. 7) is an orientation reached by rotating the lower frame 340 a predetermined angle α in the clockwise direction around the pivot axis Y from the horizontal orientation (the orientation indicated by broken lines in FIG. 7) as viewed from the inner side in the user width direction.

Here, given the movement of a left leg when a user wearing the gait motion assisting device 1 equipped with the actuator unit 100 walks, the first lower leg frame 40(1) is rotated in the clockwise direction relative to the first thigh frame 20(1) as viewed from the inner side in the user width direction.

Accordingly, in the initial orientation with the actuator unit being attached to the gait motion assisting device 1, assuming that the lower frame 340 is rotated the predetermined angle α in the clockwise direction around the pivot axis Y from a horizontal orientation (the orientation indicated by broken lines in FIG. 7) as viewed from the inner side in the user width direction, the range in which pressing force can be applied in the bending direction of the knee to assist the user's gait movement, i.e., the rotation range in which the lower frame 340 can be rotated in the clockwise direction around the pivot axis Y as viewed from the inner side in the user width direction, is reduced to an extent corresponding to the predetermined angle α in reference to the horizontal orientation.

On the other hand, attaching the actuator unit 100 such that the first lower leg frame 40(1) is sandwiched between the engagement pin 372 and the second engagement arm 375(2) positioned on the back side with respect to the user front-back direction brings the lower frame 340 into an orientation wherein the lower frame 340 is rotated the predetermined angle α in the counterclockwise direction around the pivot axis Y from the horizontal orientation (the orientation indicated by broken lines in FIG. 7) as viewed from the inner side in the user thickness direction in the initial orientation (the orientation wherein the user is in a substantially upright state).

Accordingly, the range in which pressing force can be applied in the knee bending direction to assist the user's gait movement, i.e., the rotation range in which the lower frame 340 can be rotated in the clockwise direction around the pivot axis Y as viewed from the inner side in the user width direction, can be increased to an extent corresponding to the predetermined angle α in reference to the horizontal orientation.

Here, the control structure of the gait motion assisting device 1 according to the present embodiment will now be described.

The gait motion assisting device 1 according to the present embodiment identifies a gait state during a gait cycle based on a thigh phase angle and performs operational control of the actuator unit 100 so as to impart gait assisting force suitable for the gait state.

As described above, in the present embodiment, the actuator unit 100 imparts gait assisting force to the lower leg.

That is, the gait motion assisting device 1 according to the present embodiment is configured to detect movement of the thigh, which is different from the lower leg that is a control target site, and perform operational control of the actuator unit 100 that imparts gait assisting force to the lower leg, which is a control target site, based on the movement of the thigh.

Figure 8:
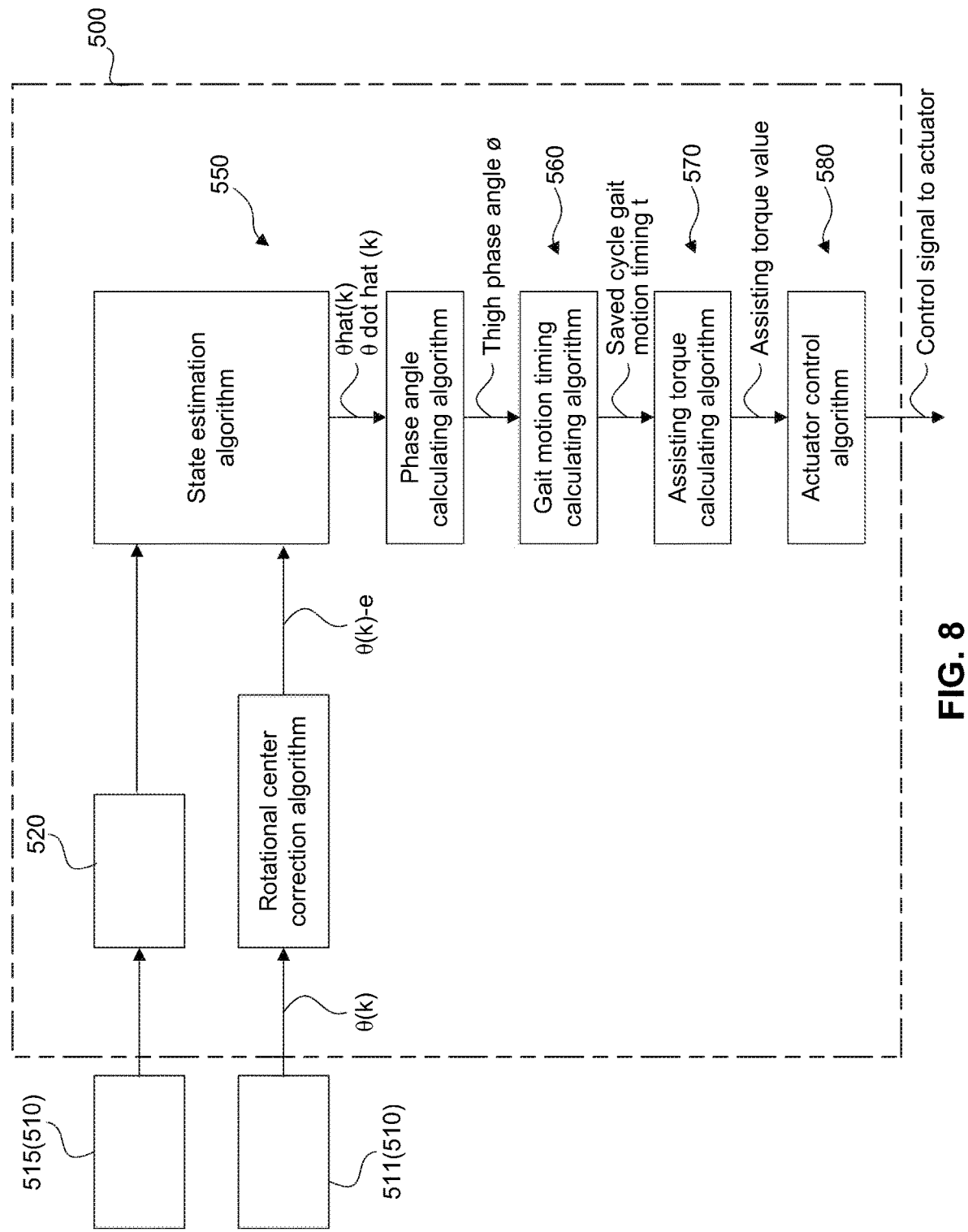
FIG. 8 is a control block diagram of the gait motion assisting device.

FIG. 8 shows a control block diagram of the gait motion assisting device 1.

As shown in FIG. 8, the gait motion assisting device 1 includes a thigh orientation detecting means 510 capable of detecting an angle-related signal relating to a hip joint angle that is a forward and backward swing angle of a user's thigh, a thigh phase angle calculating means 550 for calculating a thigh phase angle φ based on the angle-related signal, a gait motion timing calculating means 560 for converting the thigh phase angle φ into a gait state (a gait motion timing) during a gait cycle, an assisting torque calculating means 570 for calculating a torque value that should be output at the gait motion timing, and an operational control means 580 responsible for operational control of the actuator unit 100 (the driver 110).

As shown in FIG. 1, the gait motion assisting device 1 according to the present embodiment includes a control device 500.

In the present embodiment, as shown in FIG. 8, the control device 500 acts as the thigh phase angle calculating means 550, the gait motion timing calculating means 560, the assisting torque calculating means 570, and the operational control means 580.

The control device 500 has a processing unit including a control processing means for executing processing based on a signal received from the thigh orientation detecting means 510, a manually operated member, or the like; and a storage unit including a ROM for storing a control program, control data, and the like, a non-volatile storage means storing a setting value or the like such that the setting value or the like is not lost even when a power supply is interrupted and is rewritable, a RAM for temporarily storing data generated during processing by the processing unit, or the like.

The thigh orientation detecting means 510 detects the angle-related signal at each predetermined specific sampling timing during one gait cycle.

The thigh orientation detecting means 510 may have various forms such as a gyro sensor, an acceleration sensor, and a rotary encoder as long as the forward and backward swing angle of the thigh (the hip joint angle) can be directly or indirectly detected.

In the gait motion assisting device 1 according to the present embodiment, the thigh orientation detecting means 510 has a three-axis angular velocity sensor (a gyro sensor) 511 capable of detecting the forward and backward swing angular velocity of the thigh.

The gait motion assisting device 1 according to the present embodiment has a three-axis acceleration sensor 515, and the thigh phase angle calculating means 550 is configured to use a vertical axis Z detected by the three-axis acceleration sensor 515 when user stands still or does not walk as a reference axis for the hip joint angle (the forward and backward swing angle of the thigh).

Figure 9B:
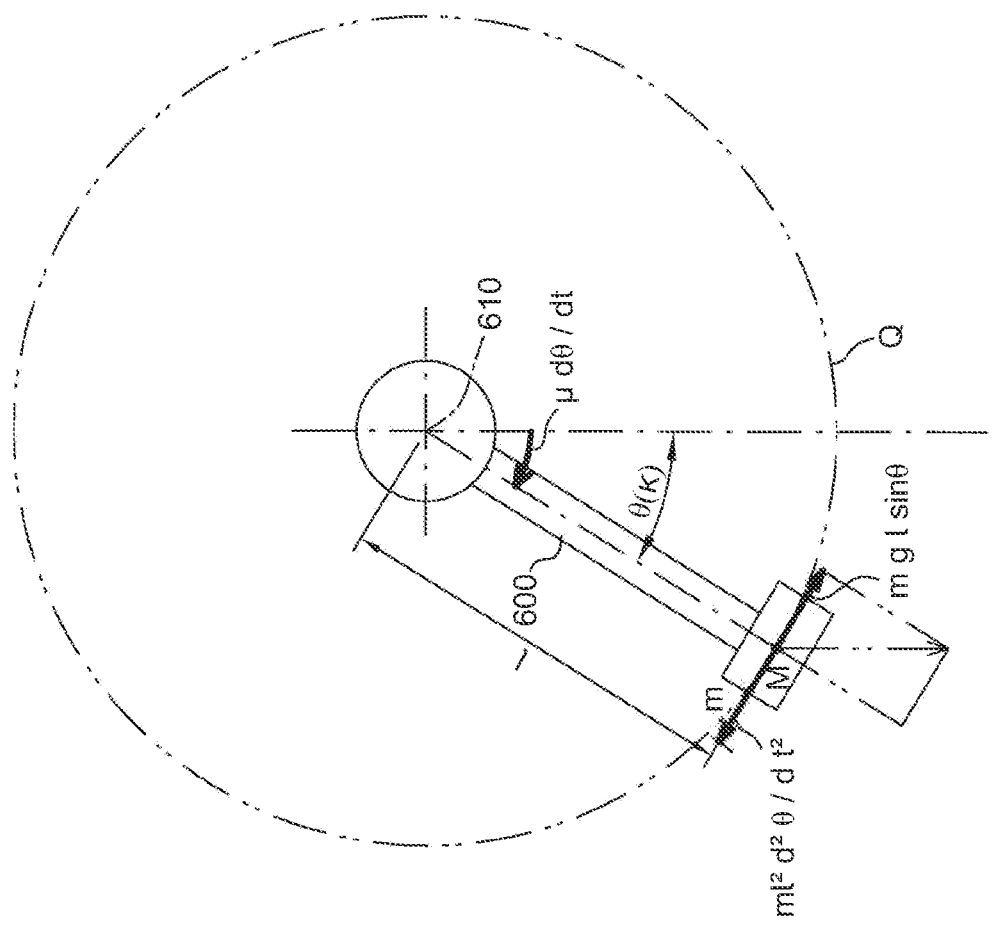
FIG. 9B is a schematic side view showing pendulum movement of rod-like rigid body that replicates movement around the hip joint of the user's leg.
Figure 9A:
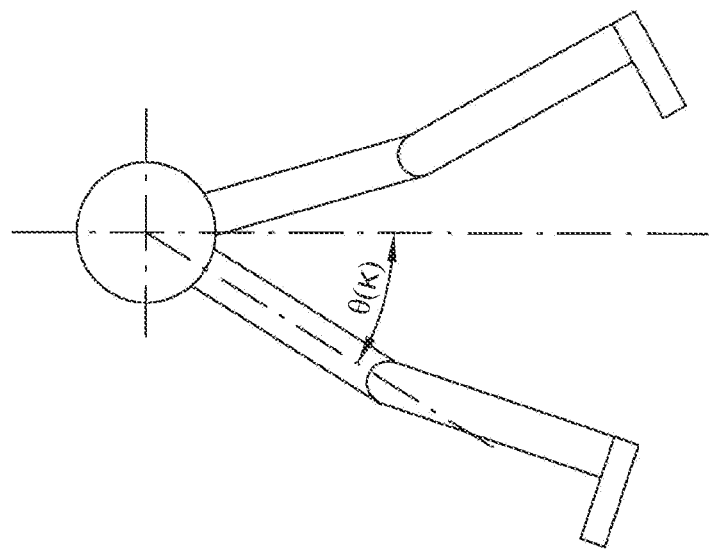
FIG. 9A is a schematic side view schematically depicting movement around a hip joint of a user's leg including a thigh and a lower leg during walking.

FIG. 9A is a schematic side view schematically depicting movement around the hip joint of a user's leg including a thigh and a lower leg during walking.

In the present embodiment, the thigh phase angle calculating means 550 is configured to replicate movement around the hip joint of a user's leg including a thigh and a lower leg during walking by pendulum movement of a rod-like rigid body 600 having a predetermined length l, the distal end part of which has a material point M with a predetermined mass m and the proximal end part of which serves as a swing center 610, as shown in FIG. 9B, and obtain an estimated hip joint angle θ hat and an estimated hip joint angular velocity θ dot hat at one sampling timing k using a state estimator designed for the equation of motion of this pendulum motion.

Note that m and l are set for each user by experimentation or the like, and the mass of the rod-like rigid body 600 is 0.

Specifically, the equation of motion of the rod-like rigid body 600 having the material point M in the direction tangential to a circle Q drawn along the swing trajectory of the material point M is represented by equation (8).

[Math. 8]

$$m\ell^2 \frac{d^2\theta(t)}{dt^2} + \mu \frac{d\theta(t)}{dt} + mg\ell^2 \sin\theta(t) = \gamma(t) \qquad (8)$$

In equation (8), θ(t) denotes a hip joint angle that is the forward and backward swing angle of a user's thigh and that is represented by the swing angle of the rod-like rigid body 600 relative to the vertical axis passing the swing center.

Also, g denotes gravitational acceleration, μ denotes a viscous friction coefficient resulting from frictional force around the swing center of the rod-like rigid body, and γ denotes unknown disturbance including the hip joint torque of a user.

Here, assuming that θ(t) falls within a relatively small swinging range, an approximation sin θ(t)=θ(t) holds. Applying this approximation, combining a user's hip joint angle θ and hip joint angular velocity θ dot that are replicated by the swing angle and the swing angular velocity of the material point M into a vector of equation (9a) below, and rewriting equation (8) using this vector result in equation (9b) below.

[Math. 9]

$$x(t) = \begin{bmatrix} \theta(t) \\ \dot{\theta}(t) \end{bmatrix} \qquad (9a)$$

$$\begin{bmatrix} \dot{\theta}(t) \\ \ddot{\theta}(t) \end{bmatrix} = \begin{bmatrix} 0 & 1 \\ -\frac{g}{\ell} & -\frac{\mu}{m\ell^2} \end{bmatrix} \begin{bmatrix} \theta(t) \\ \dot{\theta}(t) \end{bmatrix} + \begin{bmatrix} 0 \\ \frac{1}{m\ell^2} \end{bmatrix} \gamma(t) \qquad (9b)$$

Rewriting equation (9b) using vector x(t) (see equation (9a)) results in equation (10a) and equation (10b).

[Math. 10]

$$\dot{x}(t) = Ax(t) + G\gamma(t) \qquad (10a)$$

$$y(t) = Cx(t) + v(t) \qquad (10b)$$

Coefficients A and G in equation (10a) are as follows.

[Math. 6]

$$A = \begin{bmatrix} 0 & 1 \\ -\frac{g}{\ell} & -\frac{\mu}{m\ell^2} \end{bmatrix} \qquad (6)$$

[Math. 7]

$$G = \begin{bmatrix} 0 \\ \frac{1}{m\ell^2} \end{bmatrix} \qquad (7)$$

Equation (10a) and equation (10b) when expressed by a discrete time expression (a sampling timing k) give equation (1a) and equation (1b).

[Math. 1]

$$x[k+1] = Fx[k] + G_d\gamma[k] \qquad (1a)$$

$$y[k] = Cx[k] + v[k] \qquad (1b)$$

The inside of [ ] in equation (1a) and equation (1b) denotes a sampling timing.

That is, x[k+1] means the value of x at a sampling timing k+1, x[k] means the value of x at a sampling timing k, γ[k] means the value of unknown disturbance at a sampling timing k, and v[k] means the value of observation noise at a sampling timing k.

F and Gd in equation (1a) are as follows.

Meanwhile, in equation (1a), a user's muscle torque acting on the hip joint is included in unknown disturbance γ as an unknown quantity.

[Math. 4]

$$F = e^{A\Delta t} \qquad (4)$$

The right side of the above equation denotes a matrix exponential function.

[Math. 5]

$$G_d = \int_0^{\Delta t} e^{A\tau} G d\tau \qquad (5)$$

In the present embodiment, the thigh phase angle calculating means 550 uses a Kalman filter as a state estimator.

The estimate equations of a Kalman filter are expressed by equations (2a) to (2e).

[Math. 2]

$$\hat{x}[k|k-1] = F\hat{x}[k-1|k-1] \qquad (2a)$$

$$\hat{x}[k|k] = \hat{x}[k|k-1] + K[k]\{y[k] - C\hat{x}[k|k-1]\} \qquad (2b)$$

$$K[k] = P[k|k-1]C^T(CP[k|k-1]C^T + R)^{-1} \qquad (2c)$$

$$P[k|k-1] = FP[k-1|k-1]F^T + G_dQG_d^T \qquad (2d)$$

$$P[k|k] = (I - K[k]C)P[k|k-1] \qquad (2e)$$

Characters in equations (2a) to (2e) are as follows, with a superscripted character T in the equations denoting matrix transposition operation.

x hat [k|k]: Posteriori estimate at sampling timing k
x hat [k|k−1]: Priori estimate at sampling timing k
K[k]: Kalman gain at sampling timing k
P[k|k]: Posteriori error covariance matrix at sampling timing k
P[k|k−1]: Priori error covariance matrix at sampling timing k
y[k]: Observation (measure) of thigh orientation detecting means at sampling timing k
C: Observation matrix
Q: Covariance matrix of unknown disturbance γ
R: Covariance matrix of observation noise v Here, the thigh phase angle calculating means 550 calculates a Kalman gain in accordance with the sizes of an estimation error and an observation error at each sampling timing.

That is, the thigh phase angle calculating means 550 calculates a value, at which the covariance of the estimation error and the observation error is minimum, at each sampling timing according to equations (2c), (2d), and (2e), and uses this value as a Kalman gain K[k] at that sampling timing.

The Kalman filter calculates an estimated hip joint angle and an estimated hip joint angular velocity according to equations (2a) to (2e) and, at this time, the Kalman gain K[k] at a sampling timing k is calculated according to equations (2c) to (2e) at each sampling timing. Instead of calculating the Kalman gain K[k] at each sampling timing, a value K calculated according to equations (11a) and (11b) below in advance for convenience can be used as well. That is, K is used as K[k], i.e., K[k]=K.

[Math. 11]

$$K = PC^T (CPC^T + R)^{-1} \quad (11a)$$

$$F\{P - PC^T(CPC^T+R)^{-1}CP\}F^T - P + G_d Q G_d^T V = 0 \quad (11b)$$

K: Steady-state Karman gain
P: Steady-state error covariance matrix

The thigh phase angle calculating means 550 predicts a vector value x[k+1] (hereinafter referred to as a prediction) at one subsequent sampling timing k+1 based on a vector value x[k] at one sampling timing k using equation (1a).

Having obtained an optimal Kalman gain K[k] calculated at the sampling timing k or a steady-state Kalman gain K, the thigh phase angle calculating means 550 uses the prediction, which has been calculated according to equation (2a) at one previous sampling timing k−1, for one subsequent sampling timing as a priori estimate x hat [k|k−1] at the sampling timing k to calculate a posteriori estimate x hat [k|k] at the sampling timing k according to equation (2b).

The thigh phase angle calculating means 550 uses an estimated hip joint angle θ hat and an estimated hip joint angular velocity θ dot hat included in the posteriori estimate x hat [k|k] to calculate a thigh phase angle φ(k) at the sampling timing k (=Arctan(θ dot hat (k)/θ hat (k)).

According to this configuration, the following effects can be obtained.

That is, it is also possible to perform differentiation processing and low-pass processing on a hip joint angle detected by a gyro sensor or the like to obtain a hip joint angle and a hip joint angular velocity at one sampling timing, and then calculate a thigh phase angle based on this hip joint angle and hip joint angular velocity (hereinafter referred to as a comparative configuration).

However, in the comparative configuration, noise components are emphasized by differential processing and, also, performing low-pass processing results in a time delay.

On the other hand, in the present embodiment, as described above, movement of a user's leg during walking is replicated by pendulum movement of the rod-like rigid body 600, and an estimated hip joint angle θ hat and an estimated hip joint angular velocity θ dot hat at a sampling timing k are obtained using a state estimator designed for the equation of motion of this pendulum movement. Thus, the estimated hip joint angle θ hat and the estimated hip joint angular velocity θ dot hat can be obtained while effectively preventing or reducing emphasized noise components resulting from differential processing and a time delay resulting from low-pass processing.

While a Kalman filter is used as a state estimator in the present embodiment, another state estimator such as an observer is also usable instead.

As shown in FIG. 8, in the present embodiment, the thigh phase angle calculating means 550 is configured to perform a rotational center correction on a hip joint angle-related signal from the thigh orientation detecting means 510 and use a corrected hip joint angle-related signal to calculate an estimated hip joint angle θ hat and an estimated hip joint angular velocity θ dot hat.

Specifically, the thigh phase angle calculating means 550 calculates the swing center point of the estimated hip joint angle θ hat of a completed previous gait cycle to calculate the deviation of the swing center point from the hip joint angle zero point.

Then, the thigh phase angle calculating means 550 performs a correction e in accordance with the deviation on an angle-related signal received from the thigh orientation detecting means 510 during the current gait cycle, and uses a corrected angle-related signal as the observation of the state estimator.

According to this configuration, the accuracy of the phase angle φ calculated by the thigh phase angle calculating means 550 can be increased.

Gait cycles targeted when calculating the swing center point may be all gait cycles that have been completed by that time point, or may be the most recent gait cycles (e.g., 5 or 10 most recent gait cycles) among the gait cycles that have been completed by that time point.

Phase angles used when calculating the swing center point may be those of all sampling points in one calculation-target gait cycle, or may be the "positive" maximum phase angle and the "negative" minimum phase angle in one calculation-target gait cycle.

In the present embodiment, the thigh phase angle calculating means 550 is configured to plot, on a phase angle plane, thigh motion states defined by the estimated hip joint angle θ hat and the estimated hip joint angular velocity θ dot hat to prepare a trajectory diagram.

Figure 10:
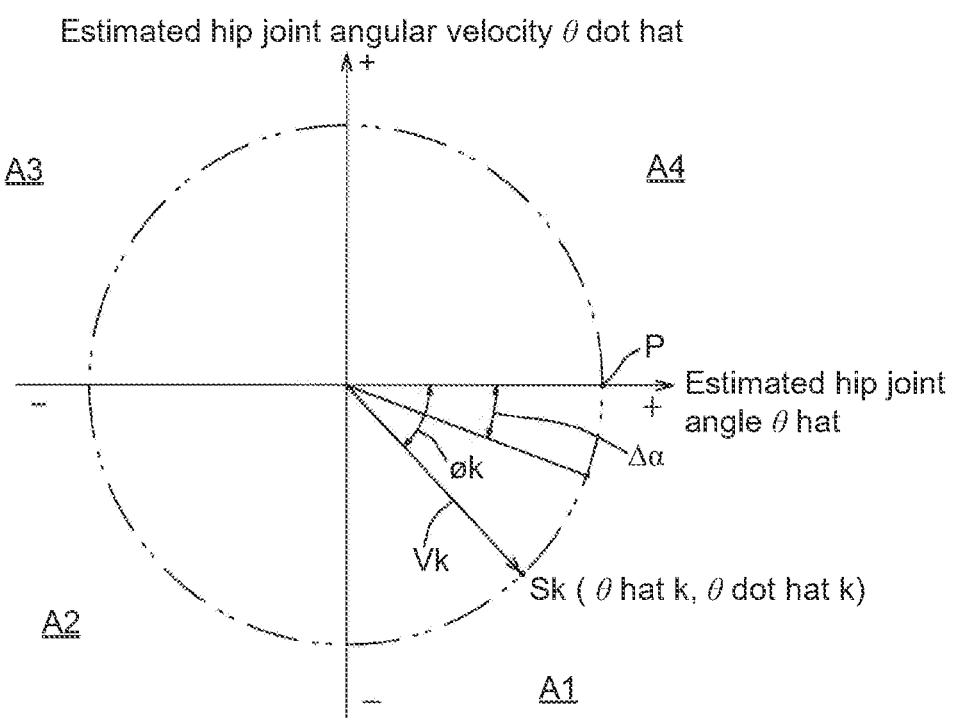
FIG. 10 is a trajectory diagram obtained by plotting estimated hip joint angles θ hat and hip joint angular velocities θ dot hat over one gait cycle, wherein estimated hip joint angles θ hat and hip joint angular velocities θ dot hat are calculated by a control device of the gait motion assisting device.

FIG. 10 shows a trajectory diagram obtained by plotting thigh motion states (gait states) defined by the estimated hip joint angle θ hat and the hip joint angular velocity θ dot hat over one gait cycle.

As shown in FIG. 10, the thigh phase angle φ determined by the estimated hip joint angle θ hat and the estimated hip joint angular velocity θ dot hat is defined so as to vary between 0 and 2Π in one gait cycle.

Specifically, the hip joint angle in a state where the thigh is positioned in front of and behind the vertical axis is referred to as "positive" and "negative", respectively, and the hip joint angular velocity in a state where the thigh is swung forward and backward is referred to as "positive" and "negative", respectively.

Under this condition, if the phase angle in a state where the estimated hip joint angle θ hat is largest in the "positive" direction and the estimated hip joint angular velocity θ dot hat is "zero" (point P in FIG. 10) is regarded as 0, a gait area A1 in FIG. 10 (a gait area from a state where the estimated hip joint angle θ hat is largest in the "positive" direction and the estimated hip joint angular velocity θ dot hat is "zero" to a state where the estimated hip joint angle θ hat is "zero" and the estimated hip joint angular velocity θ dot hat is largest in the "negative" direction) corresponds to the phase angle of 0 to Π/2.

A gait area A2 in FIG. 10 (a gait area from a state where the estimated hip joint angle θ hat is "zero" and the estimated hip joint angular velocity θ dot hat is largest in the "negative" direction to a state where the estimated hip joint angle θ hat is largest in the "negative" direction and the estimated hip joint angular velocity θ dot hat is "zero") corresponds to the phase angle of Π/2 to Π.

A gait area A3 in FIG. 10 (a gait area from a state where the estimated hip joint angle θ dot is largest in the "negative"

direction and the estimated hip joint angular velocity θ dot hat is "zero" to a state where the hip joint angle θ is "zero" and the hip joint angular velocity θ dot hat is largest in the "positive" direction) corresponds to the phase angle of π to 3Π/2.

A gait area A4 in FIG. 10 (a gait area from a state where the estimated hip joint angle θ hat is "zero" and the estimated hip joint angular velocity θ dot hat is largest in the "positive" direction to a state where the estimated hip joint angle θ hat is largest in the "positive" direction and the estimated hip joint angular velocity θ dot hat is "zero") corresponds to the phase angle of 3Π/2 to 2Π.

The sampling timing of the thigh orientation detecting means 510 is determined such that a plurality of sampling points are included in one gait cycle, and the thigh phase angle calculating means 550 calculates the thigh phase angle φ at each sampling timing.

In the present embodiment, the thigh phase angle calculating means 550 determines whether the vector length of a plot point Sk on a trajectory diagram defined by the estimated hip joint angle θ hat k and the estimated hip joint angular velocity θ dot hat k (the distance between the origin of the trajectory diagram (i.e., the point at which the estimated hip joint angle θ hat k and the estimated hip joint angular velocity θ dot hat k are zero) and the plot point Sk) exceeds a predetermined threshold value or not. When the vector length exceeds a predetermined threshold value, the thigh phase angle calculating means 550 calculates a thigh phase angle φk based on the estimated hip joint angle θ hat k and the estimated hip joint angular velocity θ dot hat k, and sends the thigh phase angle φk to the gait motion timing calculating means 560.

On the other hand, when the vector length is less than or equal to a predetermined threshold value, the thigh phase angle calculating means 550 outputs an actuator operation inhibitory signal.

This configuration makes it possible to effectively prevent the gait motion assisting device 1 from causing the actuator unit 100 to be operated when gait motion is not started.

That is, a user wearing the gait motion assisting device 1 may unintentionally change posture over a small range before starting gait motion. In particular, a user with hemiplegia or the like is likely to encounter such a situation.

When the thigh phase angle calculating means 550 has the above-described configuration, such a minor posture change is detected as a vector having a small vector length.

Accordingly, by judging that gait motion is being performed only when the vector length of a vector Vk (see FIG. 10) defined by the estimated hip joint angle θ hat k and the estimated hip joint angular velocity θ dot hat k exceeds a predetermined threshold value, it is possible to effectively prevent the actuator unit 100 from being unintentionally operated when gait motion is not started.

The gait motion timing calculating means 560 has a phase pattern function that defines the relationship between thigh phase angles φ and gait motion timings in a gait cycle, and applies a thigh phase angle φ at one sampling timing sent from the thigh phase angle calculating means 550 to the phase pattern function to calculate which gait motion timing in a gait cycle said one sampling timing corresponds to.

Moreover, every time a gait cycle is complete, the gait motion timing calculating means 560 calculates the latest phase pattern function by performing the least-squares method on effective phase angle data, which includes the latest phase angle data in which the thigh phase angle φ in the completed gait cycle is associated with a gait motion timing corresponding to the thigh phase angle and previous phase angle data stored at that time, and overwrite-saves a calculated latest phase pattern function.

Figure 11:
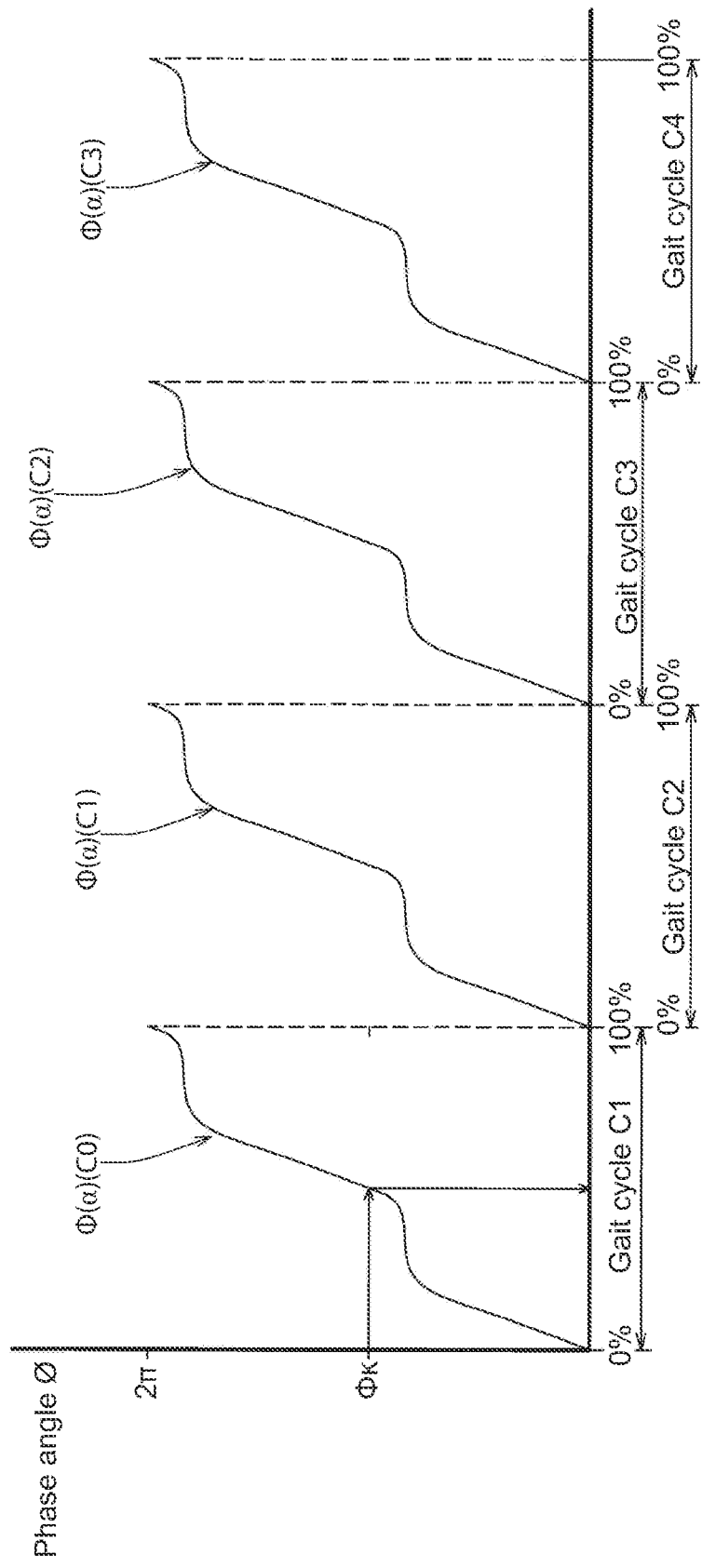
FIG. 11 is a graph obtained by plotting thigh phase angles at each gait cycle, wherein the thigh phase angles are calculated by the control device.

Specifically, as shown in FIG. 11, in the initial state, an initial phase pattern function φ(α)(C0) is saved as the phase pattern function in the gait motion timing calculating means 560.

The initial phase pattern function φ(α)(C0) is prepared for each user and stored in the gait motion timing calculating means 560 in advance.

For example, in the first gait cycle C1, the thigh phase angle calculating means 550 calculates φk as a thigh phase angle at one sampling timing Sk and sends this thigh phase angle to the gait motion timing calculating means 560.

At this time, a first gait cycle C1 is not yet completed, and thus the gait motion timing calculating means 560 has the initial phase pattern function φ(α)(C0) as the phase pattern function.

Accordingly, as shown in FIG. 11, the gait motion timing calculating means 560 applies the thigh phase angle φk sent from the thigh phase angle calculating means 550 to the initial phase pattern function φ(α)(C0) to calculate a saved cycle gait motion timing tk corresponding to said one sampling timing k, and sends this saved cycle gait motion timing tk to the assisting torque calculating means 570.

The gait motion timing calculating means 560 repeats this processing until the first gait cycle C1 is complete.

Completion of one gait cycle can be determined, for example, based on whether or not the thigh phase angle φ defined by the estimated hip joint angle θ hat and the estimated hip joint angular velocity θ dot hat has returned to a predetermined gait cycle reference angle.

When the first gait cycle C1 is complete, the gait motion timing calculating means 560 adds the latest phase angle data, in which the thigh phase angle received from the thigh phase angle calculating means 550 during the completed first gait cycle C1 is associated with a gait motion timing corresponding to the thigh phase angle, to the previous phase angle data stored at that time (in this example, phase angle data generated by the initial phase pattern function φ(α) (C0)) to prepare effective phase angle data which is effective at that time, uses the least-squares method on the effective phase angle data to calculate the latest phase angle pattern function (in this example, a phase pattern function upon first gait cycle completion φ(α)(C1)), and overwrite-saves the latest phase angle pattern function.

Specifically, when the first gait cycle C1 is complete, the gait motion timing calculating means 560 performs the least-squares method on the effective phase angle data which is effective at that time to calculate the coefficient parameter of:

$$\varphi(\alpha)(C1) = a0(1) + a1(1)\alpha + a2(1)\alpha^2 + \ldots + am(1)\alpha^m$$

and stores φ(α)(C1) as a phase pattern function of the thigh phase angle. In the above formula, m is a positive integer.

Then, in a second gait cycle C2, the gait motion timing calculating means 560 uses the phase pattern function upon first gait cycle completion φ(α)(C1) stored at that time to calculate a saved cycle gait motion timing tk.

When the second gait cycle C2 is complete, the gait motion timing calculating means 560 performs the least-squares method on the effective phase angle data which is effective at that time to calculate the coefficient parameter of:

$$\varphi(\alpha)(C2) = a0(2) + a1(2)\alpha + a2(2)\alpha^2 + \ldots + am(2)\alpha^m$$

and overwrite-saves φ(α)(C2) as a phase pattern function of the thigh phase angle.

Then, in a third gait cycle C3, the gait motion timing calculating means 560 uses the phase pattern function upon second gait cycle completion φ(α)(C2) stored at that time to calculate a saved cycle gait motion timing.

The gait motion timing calculating means 560 repeats this processing.

The effective phase angle data may include the phase angle data of all gait cycles that have been completed at that time and, alternatively, depending on the storage capacity of the gait motion timing calculating means 560, may be limited to only the phase angle data of the latest gait cycles (such as 100 gait cycles).

In the present embodiment, having the following configuration, the gait motion timing calculating means 560 prevents abnormal phase angle data from being included in the effective phase angle data used when calculating a phase angle pattern function.

That is, the gait motion timing calculating means 560 calculates a difference ΔT between the current cycle gait motion timing Tk calculated based on the thigh phase angle φk at one sampling timing k received from the thigh phase angle calculating means 550 and the saved cycle gait motion timing tk calculated by applying the thigh phase angle φk to the phase pattern function φ(α) stored at that time.

Here, the current cycle gait motion timing Tk is calculated according to:

$$Tk=(\varphi k/2\Pi)\times 100(\%)$$

When the absolute value of the difference ΔT is less than or equal to a predetermined threshold value, the gait motion timing calculating means 560 stores the current cycle gait motion timing Tk as effective phase angle data that is used when calculating a new phase pattern function φ(α) upon completion of a gait cycle.

That is, when the absolute value of the difference ΔT is less than or equal to a predetermined threshold value, the gait motion timing calculating means 560 when calculating the latest phase pattern function upon completion of one gait cycle uses the current cycle gait motion timing Tk as a gait motion timing that is to be associated with a thigh phase angle φ received from the thigh phase angle calculating means 550 in said one gait cycle.

On the other hand, when the absolute value of the difference ΔT exceeds a predetermined threshold value, the gait motion timing calculating means 560 stores the saved cycle gait motion timing tk as effective phase angle data that is used when calculating the latest phase pattern function upon completion of a gait cycle.

That is, when the absolute value of the difference ΔT exceeds a predetermined threshold value, the gait motion timing calculating means 560 when calculating the latest phase pattern function upon completion of one gait cycle uses the saved cycle gait motion timing tk as a gait motion timing that is to be associated with a thigh phase angle φ received from the thigh phase angle calculating means 550 in said one gait cycle.

This configuration makes it possible to effectively prevent the current cycle gait motion timing Tk, which has somehow become an abnormal value, from being included in the target data (effective phase angle data) which is used when calculating a phase pattern function.

The assisting torque calculating means 570 has an output torque pattern that defines the relationship between a gait motion timing and a torque value that should be output, and applies a gait motion timing sent from the gait motion timing calculating means 560 to the output torque pattern to calculate a torque value that should be output at the sampling timing Sn.

The output torque pattern is prepared for each user and is stored in the assisting torque calculating means 570 in advance.

The operational control means 580 performs operational control of the actuator unit 100 so as to output assisting force having a torque value calculated by the assisting torque calculating means 570.

Thus, the gait motion assisting device 1 according to the present embodiment is configured to identify a gait state (a gait motion timing) during a gait cycle based on a thigh phase angle φ and output assisting force corresponding to the gait state.

Accordingly, it is possible to precisely identify a gait state (a gait motion timing) and output assisting force suitable for the gait state.

Also, the gait motion assisting device 1 according to the present embodiment is configured to apply the thigh phase angle φ to a phase pattern function stored at that time to calculate a gait motion timing.

Accordingly, even when irregular gait motion is made during a gait cycle, corrected assisting force can be output.

Also, in the gait motion assisting device 1 according to the present embodiment, the thigh phase angle calculating means 550, only when the vector length of the plot point on a trajectory diagram defined by the estimated hip joint angle θ hat and the estimated hip joint angular velocity θ dot hat exceeds a predetermined threshold value, calculates a thigh phase angle φ based on the estimated hip joint angle θ hat and the estimated hip joint angular velocity θ dot hat and sends the thigh phase angle φ to the gait motion timing calculating means and, on the other hand, when the vector length is less than or equal to a predetermined threshold value, the thigh phase angle calculating means 550 outputs an actuator operation inhibitory signal.

Accordingly, in the case where a user wearing the gait motion assisting device 1 unintentionally changes posture, the actuator unit 100 can be effectively prevented from outputting gait assisting force when gait motion is not started.

Moreover, the gait motion assisting device 1 according to the present embodiment, as described above, identifies a gait state during one gait cycle based on the thigh phase angle φ and then outputs gait assisting force to the lower leg by the actuator unit 100.

Accordingly, suitable gait assisting force can be supplied even to a user with hemiplegia due to a stroke or the like.

That is, conventional gait assisting devices configured to impart gait assisting force by an actuator unit are configured to detect movement of a control target site to which assisting force is to be imparted by the actuator unit, and perform operational control of the actuator unit based on the detection result.

For example, in conventional gait assisting devices that supply gait assisting force to the thigh, operational control of the actuator that imparts gait assisting force to the thigh is performed based on the result of detecting thigh movement.

Moreover, in conventional gait assisting devices that supply gait assisting force to the lower leg, operational control of the actuator for imparting gait assisting force to the lower leg is performed based on the result of detecting lower leg movement.

However, in the case of a patient with hemiplegia due to a stroke or the like, gait motion of the lower leg (forward and backward swing motion around the knee joint) often cannot be performed normally, while gait motion of the thigh (forward and backward swing motion around the hip joint) can be performed relatively normally.

When attempting to impart gait assisting force to the lower leg of such a patient, the above conventional gait assisting devices perform operational control of the actuator, which provides gait assisting force to the lower leg, based on the movement of the lower leg that is incapable of normal gait motion and, possibly, suitable gait assisting force cannot be provided.

On the other hand, the gait motion assisting device 1 according to the present embodiment is configured to perform operational control of the actuator unit 100, which imparts gait assisting force to the lower leg, based on the thigh phase angle φ as described above.

Accordingly, suitable gait assisting force can be supplied to the lower leg even when a user has hemiplegia due to a stroke or the like.

Here, gait assisting force required for gait motion will now be described.

Figure 12:
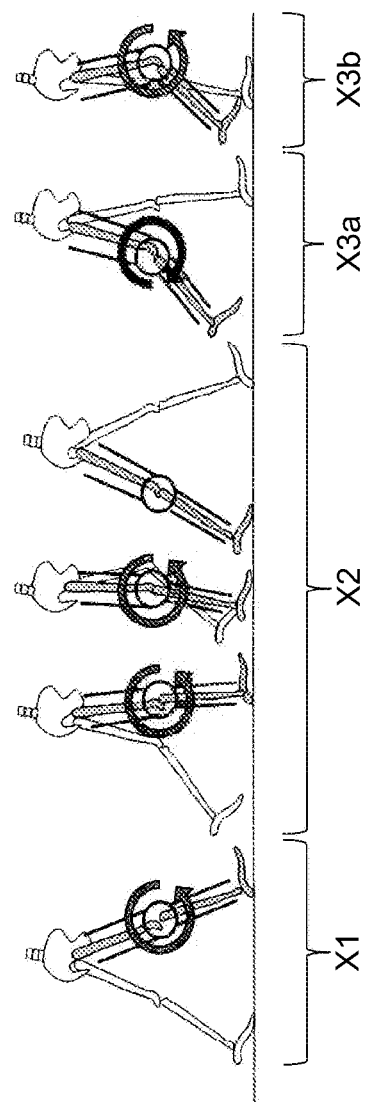
FIG. 12 is a schematic diagram showing a transition of gait states during one gait cycle.

FIG. 12 shows a schematic diagram of gait states that change during one gait cycle.

As shown in FIG. 12, one gait cycle includes a heel contact phase X1 including a heel contact time point when the heel contacts the ground in front of the vertical axis (a period before and after the forward-raised foot contacts the floor), a stance phase X2 when the heel-contacted leg after heel contact is relatively moved backward while being in contact with the ground period when the floor-contacted lower limb is relatively moved backward relative to the body), and a swing phase X3 when the leg contacting the ground is raised after the end of stance phase X2 and relatively moved forward.

Figure 13A:
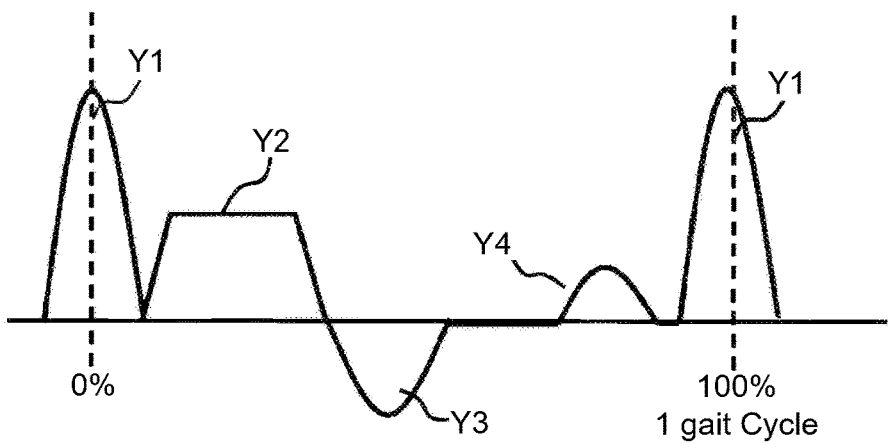
FIGS. 13A and 13B shows one example and the other example of assisting force control data that stored in the control device in advance, respectively, wherein the assisting force control date shows a relationship between gait states during one gait cycle and assisting force to be output by the actuator unit.

FIG. 13A shows one example of the change pattern of assisting force defined by the output torque pattern.

In the example shown in FIG. 13A, the output torque pattern includes a first torque pattern Y1 for preventing knee bending by rotating the lower leg-side brace 30 in the knee extending direction around the knee joint in the heel contact phase X1, a second torque pattern Y2 for preventing knee bending by rotating the lower leg-side brace 30 in the knee extending direction around the knee joint in the stance phase X2, a third torque pattern Y3 for assisting the raising of the leg by rotating the lower leg-side brace 30 around the knee joint in the knee bending direction in an initial stage X3*a* of the swing phase X2 wherein the leg contacting the ground is raised after the end of the stance phase X2 and relatively moved forward, and a fourth torque pattern Y4 for rotating the lower leg-side brace 30 around the knee joint in the knee extending direction in a later stage X3*b* of the swing phase X3.

Figure 13B:
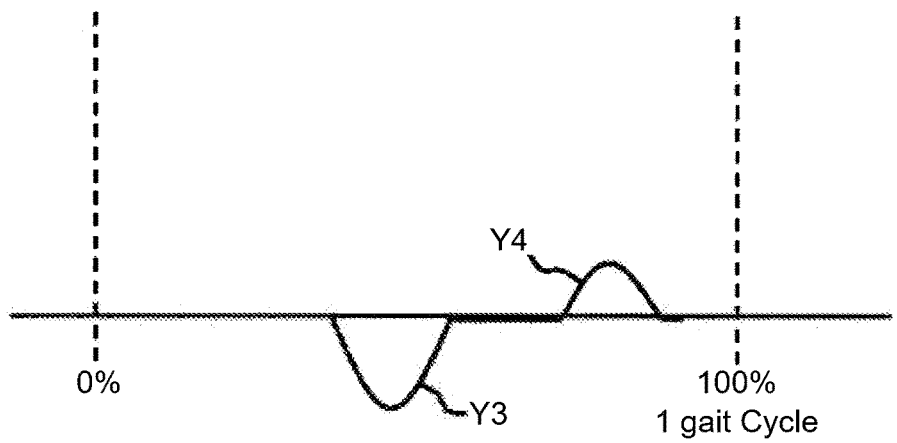

FIG. 13B shows another example of the change pattern of assisting force defined by the output torque pattern.

In the example shown in FIG. 13B, the output torque pattern includes only the third torque pattern Y3 and the fourth torque pattern Y4.

Thus, by performing operational control of the actuator unit 100 using the output torque pattern that shows the relationship between a gait state (a gait motion timing) during a gait cycle and gait assisting force, gait assistance appropriate for a user can be performed.

In the examples shown in FIGS. 13A and 13B, heel contact is set as a gait cycle reference timing.

Thus, setting heel contact as a gait cycle reference timing makes it possible to precisely identify a timing at which gait assisting force is needed during a gait cycle.

The timing of heel contact can be identified by various methods.

For example, if the hip joint angular velocity when the thigh swings forward and backward in reference to the vertical axis is referred to as positive and negative, respectively, the control device 500 can be configured to identify, as the heel contact timing, the time point at which the phase angle advances by a predetermined angle Δα from the timing (P in FIG. 10) at which the calculated hip joint angular velocity reaches zero from a positive value.

Alternatively, it is possible to provide the gait motion assisting device 1 with a heel contact detecting means for detecting heel contact, and configure the thigh phase angle detecting means to identify a timing detected by the heel contact detecting means as a heel contact time point and identify the thigh phase angle φ at that timing as a heel contact phase angle.

When the acceleration sensor 515 is provided as in the gait motion assisting device 1 according to the present embodiment, the acceleration sensor 515 can be also used as the heel contact detecting means.

Alternatively, it is also possible to separately provide a pressure sensor capable of detecting ground contact of the heel and cause the pressure sensor to act as the heel contact detecting means.

Figure 14:
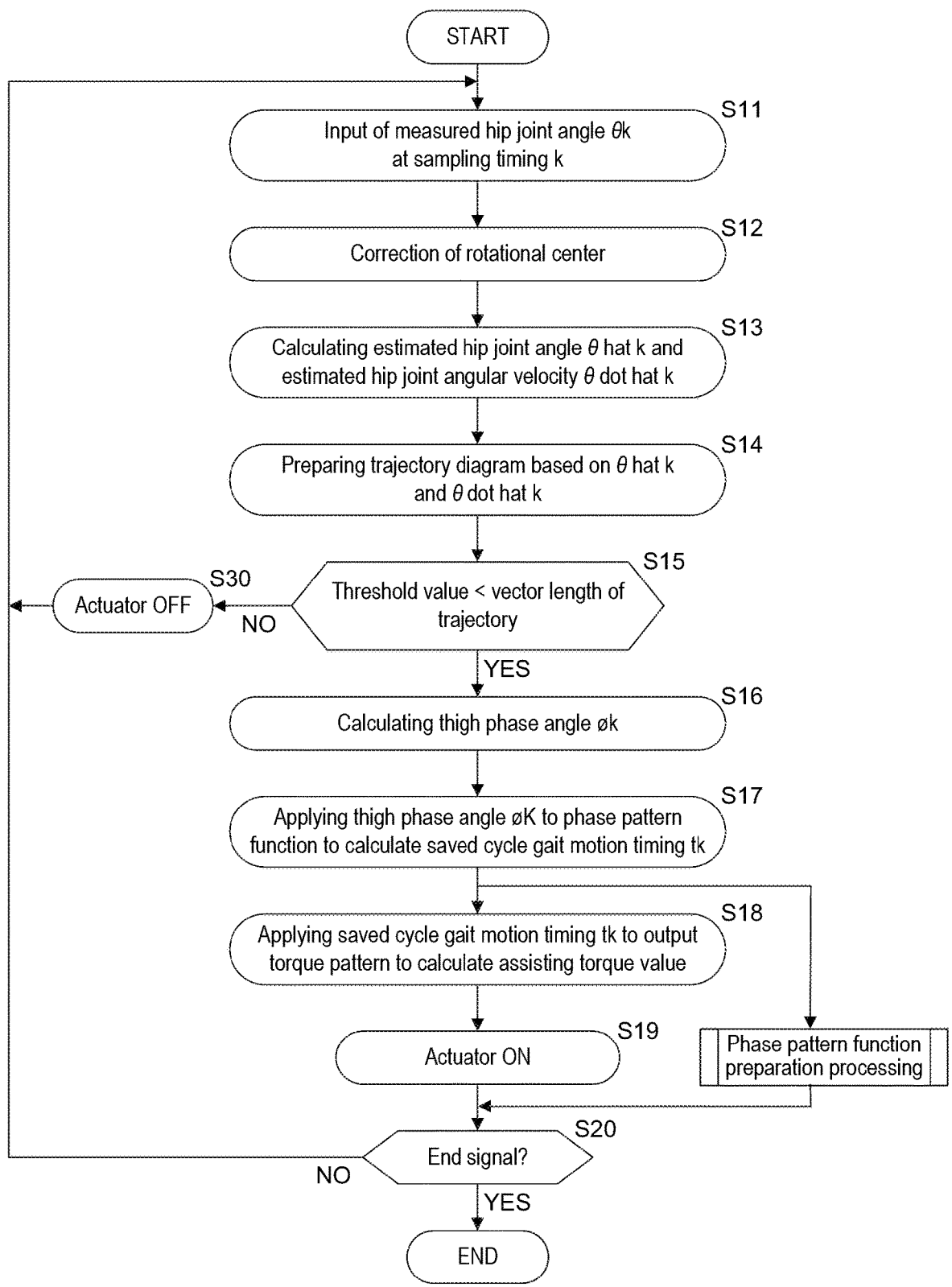
FIG. 14 is a flowchart of an actuator operational control mode performed by the control device.

FIG. 14 shows the flow of an actuator operational control mode in the gait motion assisting device 1.

The control device 500 activates the actuator operational control mode in response to input of an activation signal.

The activation signal is input in response to, for example, manual operation by a user on a manually operated member such as a start button.

When the actuator operational control mode is activated, the phase angle detecting means 550 identifies a measured hip joint angle θk at one sampling timing k based on an angle-related signal at that sampling timing k from the thigh orientation detecting means 510 (step S11).

The thigh phase angle detecting means 550 performs rotational center correction processing on the hip joint angle θk to calculate a corrected hip joint angle θk (step S12).

At a stage where no swing center is previously identified, zero correction (no correction) is performed in step 12.

The thigh phase angle detecting means 550 calculates an estimated hip joint angle θ dot k and an estimated hip joint angular velocity θ dot hat k at the sampling timing k using a state estimator (a Kalman filter in the present embodiment) designed for the equation of motion of the pendulum motion of the rod-like rigid body 600 that replicates the motion of a user's leg (step S13).

The thigh phase angle detecting means 550 prepares a trajectory diagram based on the estimated hip joint angle θ hat k and the estimated hip joint angular velocity θ dot hat k (step S14) and determines whether the vector length of a plot point on the trajectory diagram (the distance between the plot point and the origin) exceeds a threshold value (step S15).

If NO in step S15, the thigh phase angle detecting means 550 judges that gait motion is not started, and outputs an actuator operation prohibitory signal (step S30).

In this case, the actuator operation control mode returns to step S11.

If YES in step S15, the thigh phase angle detecting means 550 judges that gait motion is being performed, calculates a thigh phase angle φk based on the estimated hip joint angle θ hat k and the estimated hip joint angular velocity θ dot hat k, and sends the thigh phase angle φk to the gait motion timing calculating means 560 (step S16).

The gait motion timing calculating means 560 applies the thigh phase angle φk from the thigh phase angle detecting means 550 to a phase pattern function φ(α) effective at that time to calculate a saved cycle gait motion timing tk, and sends the saved cycle gait motion timing tk to the assisting torque calculating means 570 (step S17).

At the same time, the gait motion timing calculating means 560 executes phase pattern function preparation processing. The phase pattern function preparation processing will be described below.

The assisting torque calculating means 570 applies the saved cycle gait motion timing tk from the gait motion timing calculating means 560 to the stored output torque pattern to obtain the size and the direction of gait assisting force that should be output by the actuator unit 100 at this timing (a sampling timing k), and sends this information to the operational control means 580 (step S18).

The operational control means 580 performs operational control of the actuator unit 100 such that gait assisting force having the size and the direction calculated by the assisting torque calculating means 570 is output (step S19).

Figure 15:
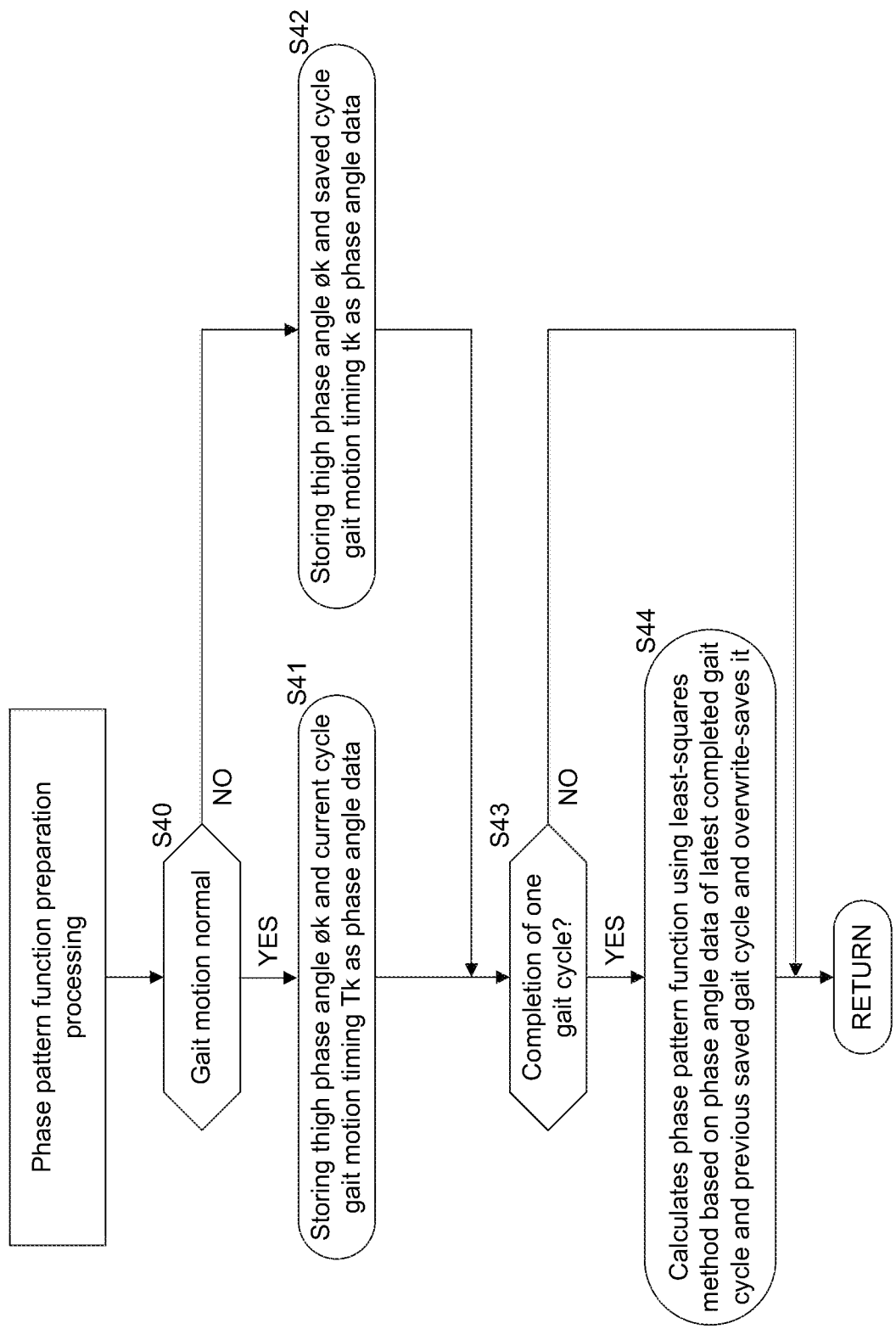
FIG. 15 is a flowchart of phase pattern function preparation processing in the flowchart shown in FIG. 14.

Here, the phase pattern function preparation processing will now be described with reference to FIG. 15.

The phase pattern function preparation processing is configured to determine whether or not the gait motion at a sampling timing k is normal, select effective phase angle data that should be used when calculating a phase pattern function used in a subsequent gait cycle, and prepare a new phase pattern function using the effective phase angle data upon completion of a gait cycle.

Specifically, in step S40, the gait motion timing calculating means 560 determines whether or not the difference ΔT between the current cycle gait motion timing Tk calculated according to $(\varphi k/2\Pi) \times 100(\%)$ and the saved cycle gait motion timing tk calculated in step S17 is less than or equal to a predetermined threshold value.

If YES in step S40, i.e., if the difference ΔT is less than or equal to a predetermined threshold value, the gait motion timing calculating means 560 judges that the gait motion at the sampling timing k is normal, and stores the thigh phase angle φk and the current cycle gait motion timing Tk as phase angle data (step S41).

On the other hand, if NO in step S40, i.e., if the difference ΔT exceeds a predetermined threshold value, the gait motion timing calculating means 560 judges that the gait motion at the sampling timing k is abnormal, and stores the thigh phase angle φk and the saved cycle gait motion timing Tk as phase angle data (step S42).

Thereafter, the gait motion timing calculating means 560 determines whether or not one gait cycle has finished (step S43) and, at the end of one gait cycle, calculates a new phase pattern function using the least-squares method based on effective phase angle data including phase angle data of that gait cycle and phase angle data of the previous saved gait cycle stored at that time, and overwrite-saves the new phase pattern function (step S44).

If one gait cycle is not yet finished, step S44 is bypassed.

The phase pattern function preparation processing makes it possible to effectively prevent data of abnormal gait motion from being included in the phase pattern function.

In step S20, the control device 500 determines whether or not an end signal for the actuator operational control mode is input and, if no end signal is input, returns to step S11, and if an end signal is input, terminates the control mode.

The end signal is input in response to, for example, a manual operation by a user on a manually operated member such as a stop button.

The gait motion assisting device 1 according to the present embodiment is configured to identify a gait motion state (a gait motion timing) based on a thigh phase angle φ and impart gait assisting force suitable for the gait motion state to the lower leg. However, the present invention is not limited to this embodiment, and the gait motion assisting device 1 may be configured to impart gait assisting force suitable for a gait motion state identified based on a thigh phase angle φ to the thigh.

DESCRIPTION OF THE REFERENCE NUMERALS

1 Gait motion assisting device
10 Thigh-side brace
30 Lower leg-side brace
100 Actuator unit
500 Control device
510 Thigh orientation detecting means
560 Gait motion timing calculating means
570 Assisting torque calculating means
580 Operational control means

The invention claimed is:

1. A gait motion assisting device comprising:
an actuator for imparting assisting force to a gait motion of a user;
a thigh orientation detecting means for detecting a hip joint angle-related signal relating to a hip joint angle that is a forward and backward swing angle of the user's thigh at each sampling timing;
a thigh phase angle calculating means for calculating a thigh phase angle at one sampling timing k;
an assisting torque calculating means having an output pattern data directly or indirectly defining a relationship between the thigh phase angle and a torque value that should be output by the actuator, wherein the assisting torque calculating means applies the thigh phase angle calculated by the thigh phase angle calculating means to the output pattern data to calculate a torque value that should be output at said one sampling timing k; and
an operational control means responsible for operational control of the actuator so as to output assisting force having the torque value calculated by the assisting torque calculating means, wherein
the thigh phase angle calculating means:
replicates movement of the user's leg including a thigh and a lower leg around a hip joint in gait motion by pendulum movement of a rod-like rigid body having a predetermined length 1, wherein a distal end part of the rod-like rigid body has a material point having a predetermined mass m and a proximal end part of the rod-like rigid body serves as a swing center,
estimates the hip joint angle and a hip joint angular velocity approximately calculated based on an equation of motion in a direction tangential to a circle drawn along a swing trajectory of the material point by a state estimator using the angle-related signal received from the thigh orientation detecting means at the sampling timing k as an observation, and
calculates the thigh phase angle at the sampling timing k using an estimated hip joint angle and an estimated hip joint angular velocity.

2. The gait motion assisting device according to claim 1, wherein
the state estimator is a Kalman filter; and
the thigh phase angle calculating means calculates the estimated hip joint angle and the estimated hip joint angular velocity using equation (1) based on the equation of motion, equation (1b) wherein the angle-related signal received from the thigh orientation detecting means is used as the observation, and equations (2a) to (2e) by the Kalman filter:

[Math. 1]

$$x[k+1] = Fx[k] + G_d \gamma[k] \tag{1a}$$

$$y[k] = Cx[k] + v[k] \tag{1b}$$

[Math. 2]

$$\hat{x}[k|k-1] = F\hat{x}[k-1|k-1] \quad (2a)$$

$$\hat{x}[k|k] = \hat{x}[k|k-1] + K[k]\{y[k] - C\hat{x}[k|k-1]\} \quad (2b)$$

$$K[k] = P[k|k-1]C^T(CP[k|k-1]C^T + R)^{-1} \quad (2c)$$

$$P[k|k-1] = FP[k-1|k-1]F^T + G_d Q G_d^T \quad (2d)$$

$$P[k|k] = (I - K[k]C)P[k|k-1] \quad (2e)$$

wherein characters in equations (1a), (1b), and (2a) to (2e) are as follows, with a superscripted character T in the equations denoting matrix transposition operation:

[Math. 3]

$$x[k] = \begin{bmatrix} \theta[k] \\ \dot{\theta}[k] \end{bmatrix} \quad (3)$$

[Math. 4]

$$F = e^{A\Delta t} \quad (4)$$

[Math. 5]

$$G_d = \int_0^{\Delta t} e^{A\tau} G \, d\tau \quad (5)$$

[Math. 6]

$$A = \begin{bmatrix} 0 & 1 \\ -\dfrac{g}{\ell} & -\dfrac{\mu}{m\ell^2} \end{bmatrix} \quad (6)$$

[Math. 7]

$$G = \begin{bmatrix} 0 \\ \dfrac{1}{m\ell^2} \end{bmatrix} \quad (7)$$

θ: Hip joint angle
θ dot: Hip joint angular velocity
g: Gravitational acceleration
μ: Hip joint torque acting around hip joint during walking
γ: Unknown disturbance
v: Observation noise
x hat [k|k]: Posteriori estimate at sampling timing k
x hat [k|k−1]: Priori estimate at sampling timing k
K[k]: Kalman gain at sampling timing k
P[k|k]: Posteriori error covariance matrix at sampling timing k
P[k|k−1]: Priori error covariance matrix at sampling timing k
y[k]: Observation (measure) of thigh orientation detecting means at sampling timing k
C: Observation matrix
Q: Covariance matrix of unknown disturbance y
R: Covariance matrix of observation noise v.

3. The gait motion assisting device according to claim 1, wherein the thigh phase angle calculating means calculates a deviation between a swing center point of the estimated hip joint angle in a completed previous gait cycle and a hip joint angle zero point, performs a correction in accordance with the deviation on the angle-related signal received from the thigh orientation detecting means during a current gait cycle, and uses a corrected angle-related signal as the observation of the state estimator.

4. The gait motion assisting device according to claim 1, comprising a thigh-side brace to be attached to the user's thigh, and a lower leg-side brace to be attached to the user's lower leg so as to be rotatable around the user's knee joint, wherein
 the actuator is attached to the thigh-side brace and is capable of imparting assisting force around the knee joint to the lower leg-side brace.

* * * * *